United States Patent [19]

Conway et al.

[11] Patent Number: 5,098,379
[45] Date of Patent: Mar. 24, 1992

[54] CATHETER HAVING LUBRICATED OUTER SLEEVE AND METHODS FOR MAKING AND USING SAME

[75] Inventors: Anthony J. Conway; Philip J. Conway, both of Chatfield; Richard D. Fryar, Jr., Rochester, all of Minn.

[73] Assignee: Rochester Medical Corporation, Stewartville, Minn.

[21] Appl. No.: 487,422

[22] Filed: Mar. 1, 1990

Related U.S. Application Data

[63] Continuation-in-part of Ser. No. 462,832, Jan. 10, 1990.

[51] Int. Cl.$^5$ ............................................. A61M 31/00
[52] U.S. Cl. ...................................... 604/51; 604/96; 604/265
[58] Field of Search ................. 604/51, 54, 55, 93, 604/96, 112, 264, 265, 270, 280, 282; 427/2

[56] References Cited

U.S. PATENT DOCUMENTS

| | | |
|---|---|---|
| 2,043,630 | 6/1936 | Raiche . |
| 2,230,226 | 4/1941 | Auzin . |
| 2,248,934 | 7/1941 | Auzin . |
| 2,308,484 | 1/1943 | Auzin et al. . |
| 2,314,262 | 3/1943 | Winder . |
| 2,322,858 | 6/1943 | Limbert et al. . |
| 2,330,399 | 9/1943 | Winder . |
| 2,330,400 | 9/1943 | Winder . |
| 2,390,070 | 12/1945 | Auzin . |
| 2,481,488 | 9/1949 | Auzin . |
| 2,690,595 | 10/1954 | Raiche . |
| 2,712,161 | 7/1955 | Moss . |
| 3,169,527 | 2/1965 | Sheridan ..................... 604/265 X |
| 3,394,705 | 7/1968 | Abramson . |
| 3,409,016 | 11/1968 | Foley . |
| 3,556,294 | 1/1971 | Walck, III et al. . |
| 3,593,713 | 7/1971 | Bogoff et al. ................... 604/265 X |
| 3,606,889 | 9/1971 | Arblaster . |
| 3,683,928 | 8/1972 | Kuntz . |
| 3,695,921 | 10/1972 | Shepherd et al. . |
| 3,699,956 | 10/1972 | Kitrilakis et al. ............... 604/265 X |
| 3,854,483 | 12/1974 | Powers . |
| 3,879,516 | 4/1975 | Wolvek . |
| 3,894,540 | 7/1975 | Bonner, Jr. . |
| 4,062,363 | 12/1977 | Bonner, Jr. . |
| 4,133,303 | 1/1979 | Patel . |
| 4,149,539 | 4/1979 | Cianci . |
| 4,196,731 | 4/1980 | Laurin et al. . |
| 4,198,984 | 4/1980 | Taylor . |
| 4,249,535 | 2/1981 | Hargest, III .......................... 604/54 |
| 4,269,310 | 5/1981 | Uson . |
| 4,381,008 | 4/1983 | Thomas et al. . |
| 4,472,226 | 9/1984 | Redinger et al. . |

(List continued on next page.)

OTHER PUBLICATIONS

The Bard Hospital Division Brochure (copyright on a date unknown prior to Nov. 9, 1989 by C. R. Bard, Inc., Murray Hill, N.J. 07974).

*Primary Examiner*—John D. Yasko
*Assistant Examiner*—Adam J. Cermak
*Attorney, Agent, or Firm*—Merchant, Gould, Smith, Edell, Welter & Schmidt

[57] ABSTRACT

An elongated catheter having an interior and an exterior surface, wherein the interior surface defines a lumen passing through the catheter. The catheter further including an enclosed cavity between the interior and exterior surfaces which encircles of the lumen. The cavity having an inner wall and an outer wall, the outer wall being a resilient sleeve which can stretch generally independently of the inner wall. The cavity containing an amount of a suitable lubricating substance effective to permit the resilient sleeve to slide along an outer surface of the inner wall while in lubricated contact therewith when stretched independently of the inner wall, wherein the inner wall and the outer wall are joined together at distal end proximal ends of the enclosed cavity. An automated method for producing the same, including a series of automated dipping steps, is also disclosed. A "Foley" catheter having a balloon portion and a lubricated resilient sleeve, as disclosed above, is also disclosed, as are methods for manufacturing the same.

29 Claims, 10 Drawing Sheets

| | | | | | |
|---|---|---|---|---|---|
| 4,571,239 | 2/1986 | Heyman . | 4,652,259 | 3/1987 | O'Neil . |
| 4,571,240 | 2/1986 | Samson et al. . | 4,664,657 | 5/1987 | Williamitis et al. . |
| 4,601,713 | 7/1986 | Fuqua . | 4,687,470 | 8/1987 | Okada . |
| 4,612,337 | 9/1986 | Fox, Jr. et al. . | 4,692,152 | 9/1987 | Emde .................................. 604/164 |
| 4,622,033 | 11/1986 | Taniguchi . | 4,710,181 | 12/1987 | Fuqua . |
| 4,623,329 | 11/1986 | Drobish et al. ........................ 604/29 | 4,737,219 | 4/1988 | Taller et al. . |
| 4,627,844 | 12/1986 | Schmitt . | 4,775,371 | 10/1988 | Mueller, Jr. . |
| 4,634,433 | 1/1987 | Osborne . | 4,863,424 | 9/1989 | Blake III et al. ..................... 604/54 |

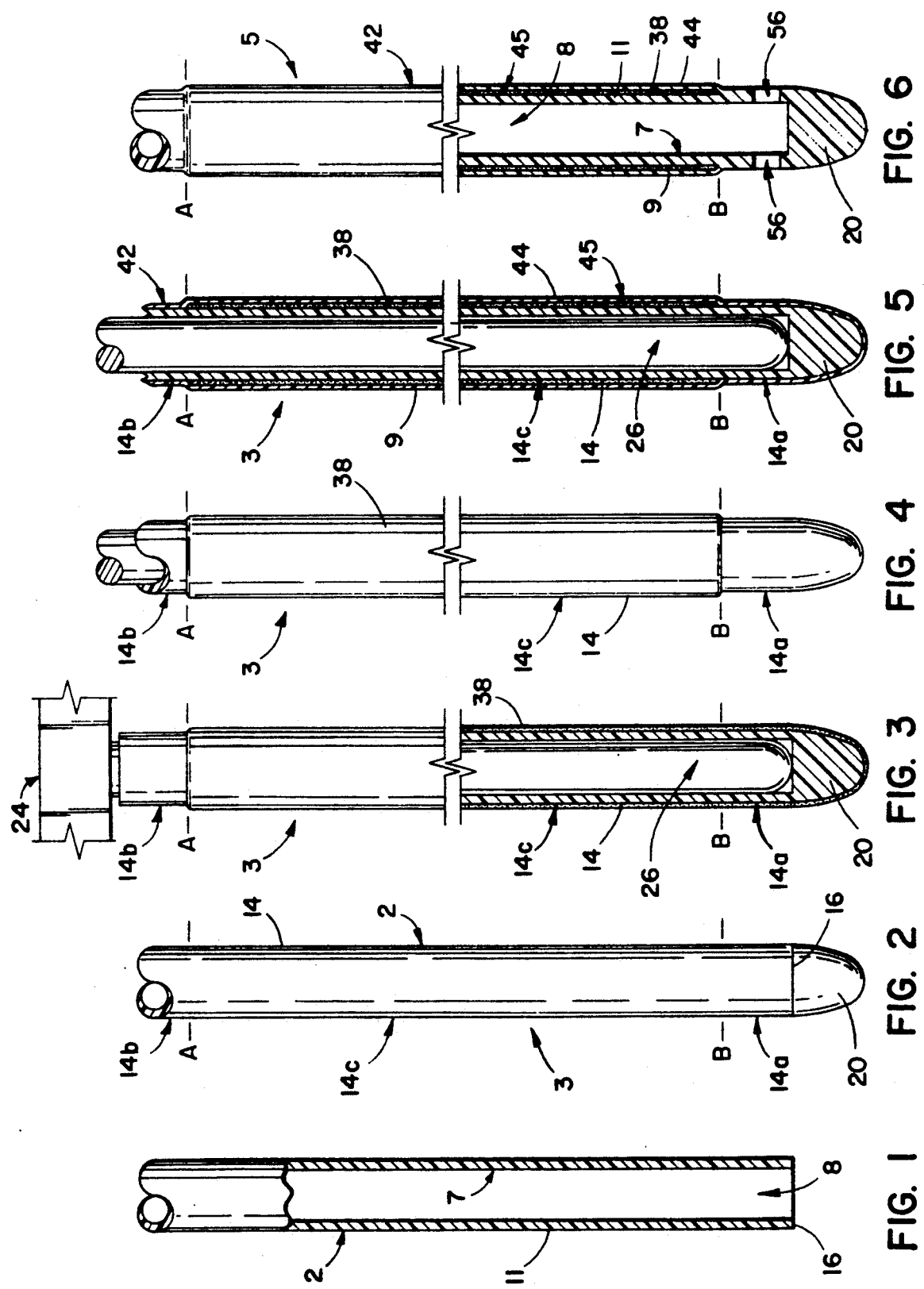

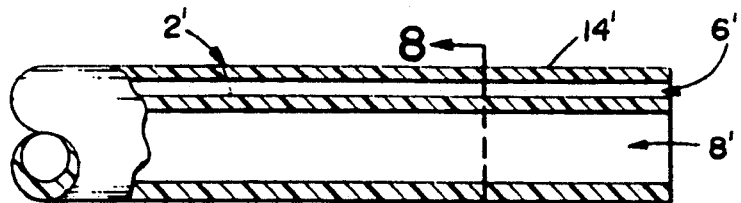 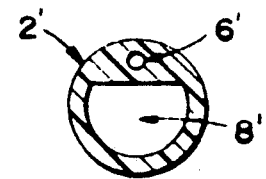
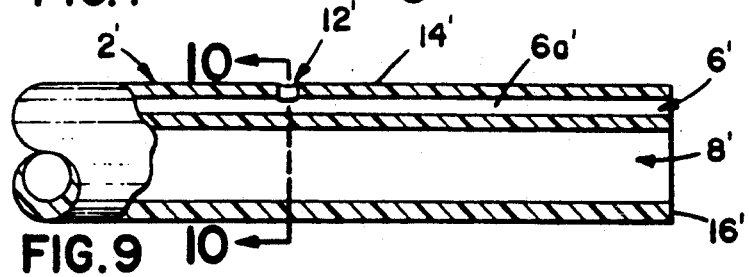 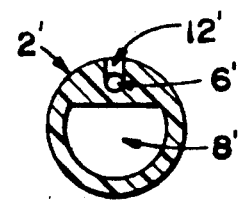
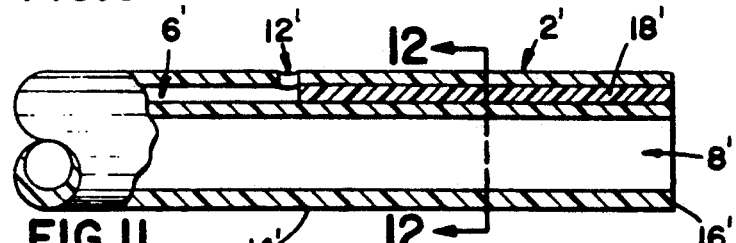 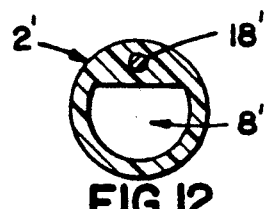
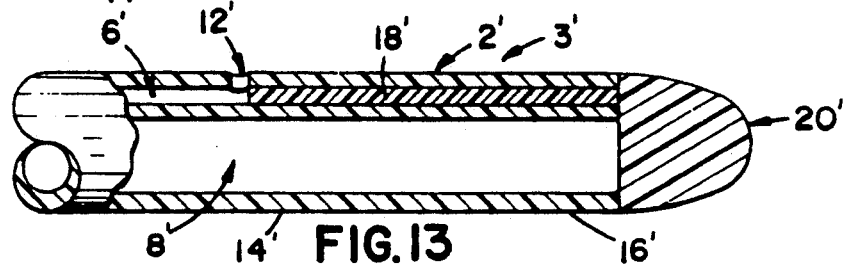
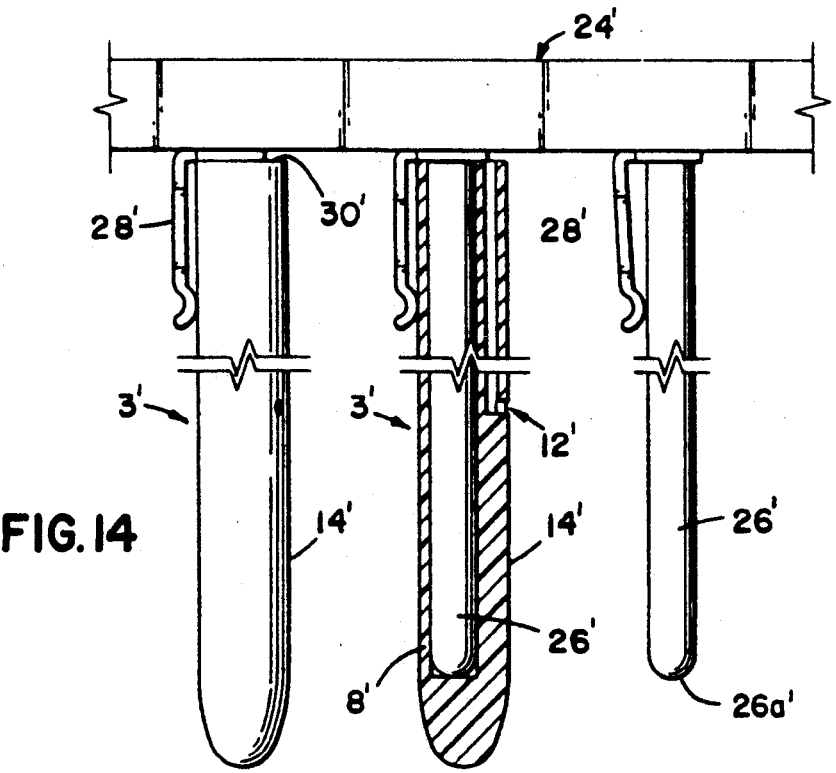

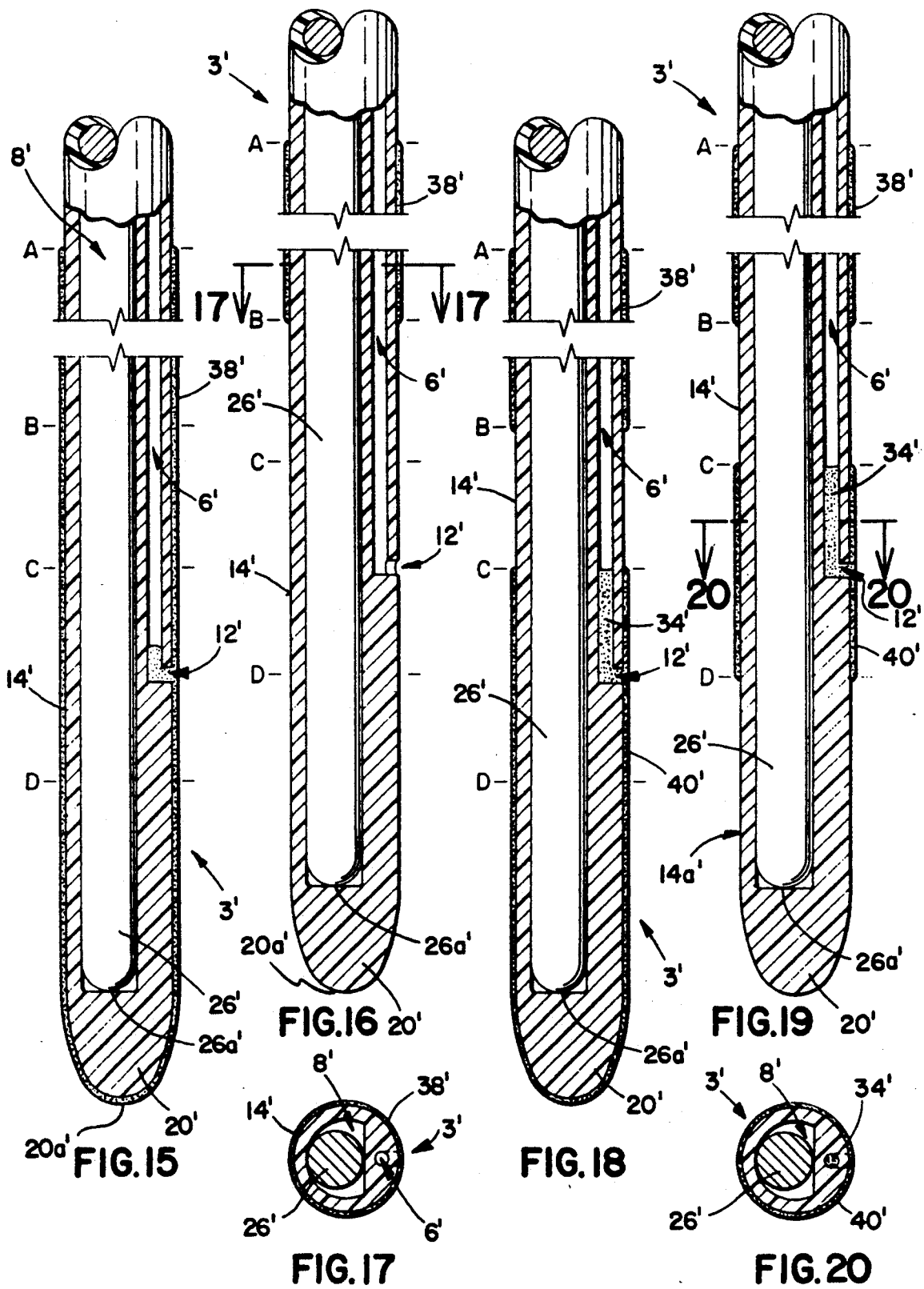

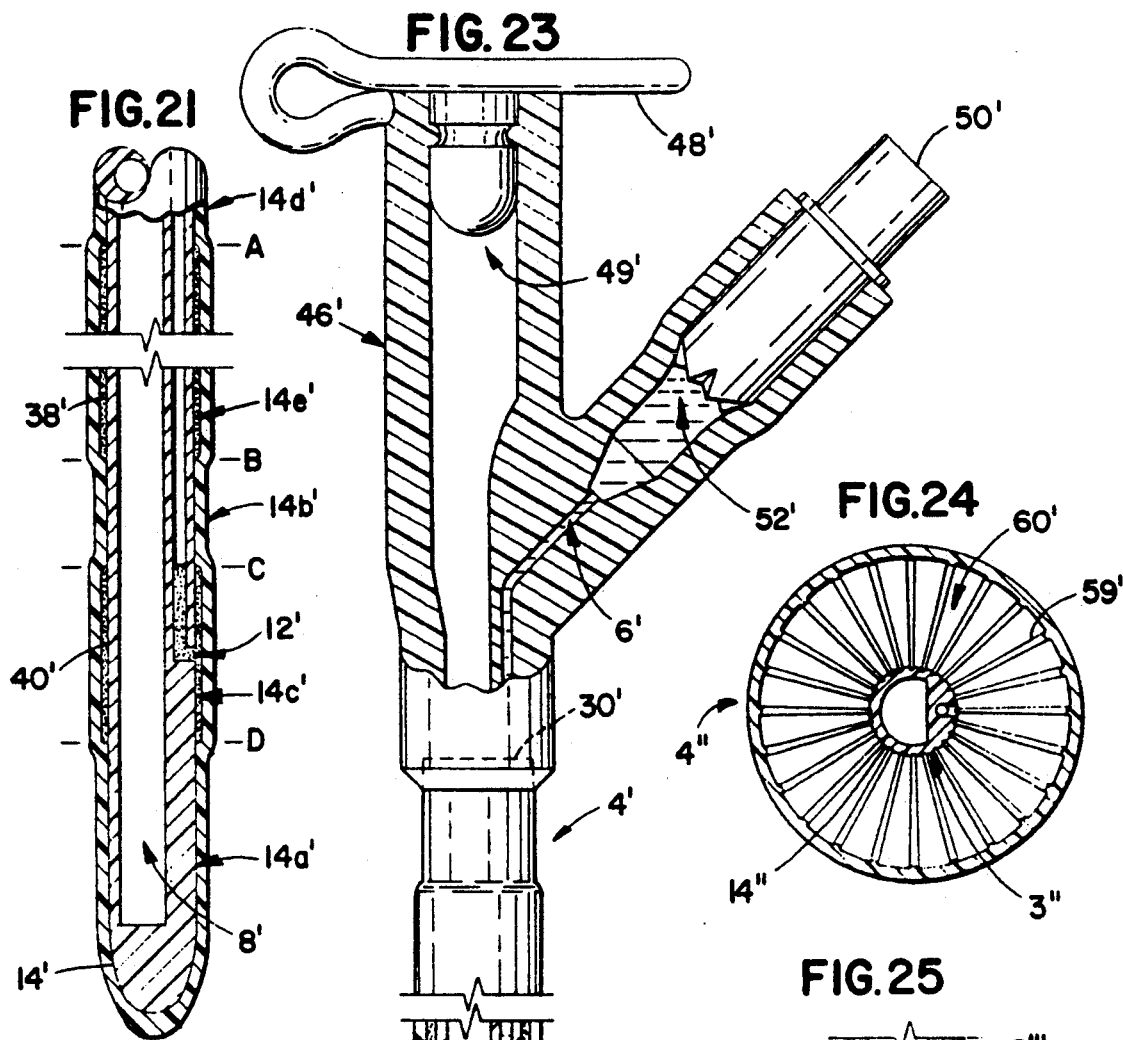
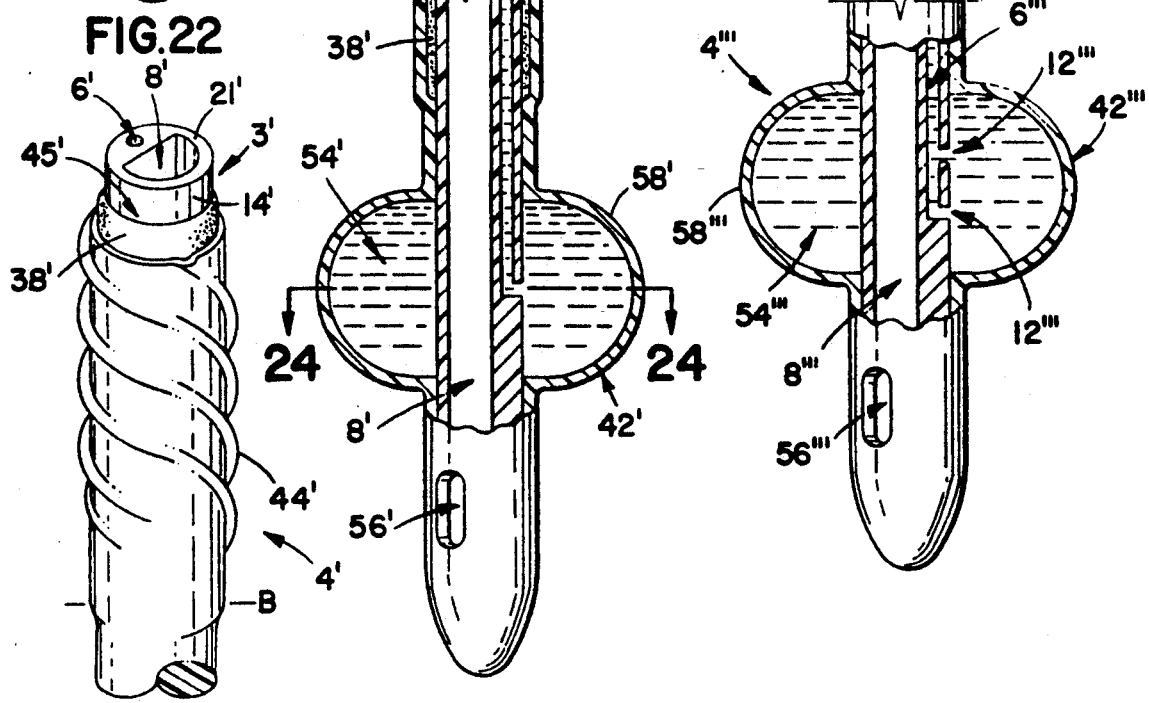
FIG.21 FIG.23 FIG.24 FIG.22 FIG.25

CATHETER HAVING LUBRICATED OUTER SLEEVE AND METHODS FOR MAKING AND USING SAME

CROSS-REFERENCE TO OTHER APPLICATIONS

The present application is a continuation-in-part application of co-pending U.S. patent application Ser. No. 462,832 filed Jan. 10, 1990, the disclosure of which is incorporated herein by reference.

FIELD OF THE INVENTION

The present invention relates to catheters for insertion into body cavities or the like and having outer sleeves which are lubricated so that they can slide, independent of other portions of the catheter, along a lubricated surface of the catheter. The present invention also relates to methods for making the same and products made by the inventive methods.

BACKGROUND OF THE INVENTION

Most catheters can be described as some sort of tube like device which is inserted into a portion of a person's body in order to transport fluids or gases in or out of that particular portion of the body. In passing through any particular portion of the body in order to reach its destination, the catheter will come into contact with various tissues in the body. For example, a catheter used to drain one's bladder (such as a "Foley" catheter) must pass through the urethral tract in order to reach the bladder. A nasograstric catheter must pass through the nasal passageway and the esophagus in order to reach the stomach. Some catheters, such as these, are inserted through existing passageways in order to reach their destinations, while others are inserted through surgically created passageways.

In virtually every catheterization, there is a significant potential for irritation of the tissues which come into contact with the catheter as the catheter is inserted and as it is withdrawn from the respective body cavity, passageway or body portion. In addition, there is a significant potential for irritation of the tissues in contact with the outer surfaces of the catheter during the period of time when the catheter resides within the respective passageway occupied by the catheter. This can be a very painful problem for the patient who must live with the irritation caused by the catheter as it rubs against the adjacent tissues in the respective passageway.

The rubbing and chafing which normally occurs is usually caused by unavoidable slight movements of the catheter tube resulting from movement of the patient. It will be appreciated that various portions of the catheter are often connected with equipment outside of the body which may or may not move in response to the movement to the body. When the patient moves the catheter must also move in reaction to the movement of the portions of the body to which it is engaged. Such movements may conflict with the lack of movement of an apparatus outside of the body to which the catheter is connected, or movement of different body portions may cause movement of the catheter with respect to one or both of the respective body portions which is inconsistent with the maintenance of relative spacial contact with outer surfaces of the catheter in one or both of the respective body portions. Simply put, body movement generally causes slight twists, pulls and/or pushes on the catheter which can rub, irritate and chafe against the tissues in the respective adjacent passageway or body portion.

It will be appreciated that this creates a great deal of discomfort for the patient who must be catheterized. In many situations, the most uncomfortable aspect of being hospitalized can be the fact that the patient must be catheterized for a significant period of time during his or her hospital stay. The catheter can be so irritating to one's adjacent tissues that the patient may become relatively tense and rigid because of their fear of movement which will result in further irritation of already irritated and sore tissues in areas adjacent to the catheter. This can virtually incapacitate a patient when the tissues become so sore that any movement causes significant pain and discomfort. It is also noted that irritated tissues are believed to be more susceptible to infection problems, so that irritation of the respective tissues adjacent to the catheter can cause an increase in the risk of infection which accompanies the patients discomfort.

The use of a nasogastric catheter is perhaps the most obvious example of the problem. After the patient has been catheterized for several days, the nasal passageway and the throat invariably become sore. The slight rubbing of the tube inside these passageways each time the patient moves his or her head or body, causes extreme discomfort once the tissues have become irritated by previous rubbing and chafing against the catheter. Often, the passageway remains sore for a significant period of time after the catheter has been removed, and is a significant source of discomfort during the hospitalization or treatment.

Accordingly, it will be appreciated that there is a need for a catheter which will address this and other problems associated with the prior art catheters. The present invention provides advantages over the prior art catheters and over the prior art methods for manufacturing catheters, and also offers other advantages over the prior art and solves other problems associated therewith.

SUMMARY OF THE INVENTION

Accordingly, it is an object of the present invention to provide an elongated catheter comprising an interior surface and an exterior surface. The interior surface defines a lumen passing through the catheter. The catheter further includes an enclosed sleeve cavity between the interior and exterior surfaces which encircles a portion of the lumen. The sleeve cavity has an inner wall and an outer wall, wherein the outer wall is a resilient sleeve which can stretch generally independently of the inner wall and the cavity contains an amount of a suitable lubricating substance effective to permit the sleeve to slide along an outer surface of the inner wall while in lubricated contact therewith when stretched independently of the inner wall, wherein the inner wall and the outer wall are joined together at distal and proximal ends of the sleeve cavity.

It will be appreciated that the resilient sleeve of the present catheter will allow the portion of the catheter defining the lumen to move independently of the exterior surface of the catheter proximate the sleeve cavity, so that when the catheter is forced to move in response to movement of a portion of the body, the resilient sleeve of the catheter will not necessarily have to move with the movement of the other portions of the catheter. When an end of the catheter moves in response to the movement of a certain portion of the body, for example, the resilient sleeve of the outer wall can stretch and twist to stay in the same relative contact with or adherence to proximate or adjacent body tissues, while the inner wall and the lumen are permitted to move in to the respective adjacent body tissues without disrupting the relative contact or adherence existing between the exterior surface of the resilient sleeve and these adjacent body tissues. Therefore, when the catheter is pulled, pushed or twisted, the resilient sleeve can stretch so that the movement of the rest of the catheter will not necessitate relative displacement of the adjacent tissues in respect to the exterior surface proximate the sleeve, because the sleeve can stretch and stay in the same position with respect to the adjacent tissues, thereby reducing the potential for rubbing, chafing and irritation of these tissues.

The present invention offers substantial improvements over the prior art. Some of these improvements relate to the comfort provided by the sleeved catheters of the present invention, while others have to do with the automated catheter manufacturing methods, the preferred materials used to make the catheters, the price of the present catheters in view of the methods and materials used, and the like. Many of the advantages of the automated manufacturing process are similar to those enumerated in co-pending U.S. patent application Ser. No. 462,832 which is incorporated herein by reference. The lubricated sleeve, however, is disclosed in the present application for the first time, and is believed to provide significant advantages over the prior art devices as will be evident from the discussion below.

Foley-type self retaining catheters provide an artificial conduit from the bladder to an external collection device. Prior art Foley catheters generally consist of a round bilumen tube which serves as a "drainage pipe" from the bladder to the external collection device. The urethral tract itself, which is generally less than two inches long in women and several inches long in men, is actually believed to be a fairly flat ribbon-shaped passageway. When Foley catheters are inserted into the bladder via the urethra, the catheter is generally forced into the urethra so as to force the ribbon-shaped passageway to open and to remain open for as long as the patient is catheterized. To avoid the problem of having urine drain down the outside of the catheter within the urethral passageway, it is standard practice to use a catheter of sufficient diameter so that it will "fill" the passageway. Therefore, it is common practice to pick a catheter which has a large enough outside diameter to hold the urethra "wide open". In order to do this, it is necessary to pick a catheter which has an outside diameter which is the same size as the size of the passageway when it is fully open. Unfortunately, the tissues of the urethral tract include soft, sensitive tissue which often becomes sore and irritated as the catheter, which is formed to the human body, rubs and chafes against it. Apart from the sheer discomfort involved, it is also noted that the outer surfaces of the irritated and sore tissues are more readily colonized by bacteria than are healthy tissues. This can result in more frequent bacterial infections from catheterizations of the urethral passageway and the bladder. Because long term catheterization is common, particularly for elderly patients who are incontinent, this is a significant problem. The present sleeved catheters, which include a resilient sleeve which can move independently of other portions of the catheter, particularly the main portion of the catheter surrounding the interior lumen or lumens, can provide significant relief in respect to the physical stress upon the body tissues adjacent to the catheter, particularly those of the urethral tract in contact with a sleeved Foley catheter of the present invention. Instead of the stiff, unforgiving exterior surface of a prior art catheter which is relatively unyielding in respect to the adjacent body tissues, the present invention includes an exterior surface which yields to the adjacent body tissues with which it is in contact when other portions of the catheter are moved. The exterior surface of the present invention includes a resilient sleeve which, in preferred embodiments, surrounds a significant amount of a cushioning or a lubricating substance which enables the resilient sleeve to provide the surrounding adjacent body tissues with a soft, "cushy" collar around the catheter which reduces mechanical stress on these adjacent body tissues.

The present invention reduces stress on the adjacent body tissues in the following ways. The conduit portion of the catheter can be moved and twisted independently of the exterior surface of the resilient sleeve portion of the sleeved catheter. Normal patient activity will cause both external and internal pressures on the catheter which will bias it toward movement in one direction or another. Since the thin resilient sleeve is separated from the main conduit portion of the catheter by a cushioning substance, preferably a lubricating gel or the like, it can easily move, stretch, compress and the like independently of the less flexible main conduit portion of the catheter which surrounds the lumen or lumens thereof. It is important to appreciate that this works in two ways. If body movements cause urethral pressures or motion the comfort sleeve will, with negligible resistance, adjust its shape and position to conform to these movements without resistance or movement of the main conduit portion of the catheter. Conversely, external movement of the main conduit portion of the catheter, such as twisting, stretching, bending and the like, can take place essentially independently of the thin resilient sleeve of the exterior surface. Thus, the mechanical stresses at the tissue/catheter interface are greatly reduced. In addition, in preferred embodiments where the thickness of the lubricating substance or gel is maximized to increase the volume of the sleeve cavity between the resilient sleeve and the main conduit portion of the catheter, the resilient sleeve is able to conform to the actual shape of the passageway through which it extends when inserted into the body. This is preferred over the generally non-compliant cylindrical tube which most catheters provide. For example, prior art Foley catheters inserted into the urethra put unnatural and unbalanced pressures on the tissues of the urethral wall as it holds the urethra open. The cushioned sleeve of preferred embodiments of the present invention, on the other hand, will provide an exterior surface which is soft and compliant. This surface will conform to the surfaces of the adjacent body tissues with which it comes into contact. In this way, the preferred catheters of the present invention will conform to the natural shape of the catheterized passageway in which it resides. In addition, it is also important to note that the present invention also provides preferred catheters which will enable health care professionals to provide patients with catheters which are more accurately sized for the passageway in which they are to be inserted. For instance, most women are fitted with Foley-type self-retaining catheters having outside diameters of 16, 18, and 20 French. On the other hand, the compliance nature of the resilient sleeve of preferred sleeved Foley catheters of the present invention allows the displacement of a portion of the volume in the sleeve cavity, which provides a cushion to the resilient sleeve, to be displaced by portions of the urethral track where it flattens out. Therefore, the preferred embodiments of the present invention will provide an exterior surface which can have a variable outside diameter so as to accommodate urethral tracts having different requirements. Furthermore, the preferred embodiments of the present invention will be more likely than the non-compliant prior art devices to accommodate variations in the wall of the urethral tract. Also, once properly fitted with a preferred embodiment of the present invention, the conduit portion of the catheter will be able to slide back and forth without disrupting the interface between the exterior surface proximate the resilient sleeve and the adjacent body tissues of the passageway in which the catheter resides.

It will be appreciated that catheters having different sleeve cavity volumes will be needed for different applications. It will be extremely advantageous for the lubricating substance in the sleeve cavity of certain preferred embodiments to be of sufficient thickness that this substance significantly separates the resilient outer sleeve from the outer wall of the conduit portion of the catheter so that the outer sleeve, when inserted in or when residing in a body passageway, will be soft and compliant such that the exterior surface proximate the resilient sleeve will provide accommodation to the differences in the shape of the orifice and the remaining portions of the passageway and will provide a "cushioned", soft interface between the adjacent body tissues and the preferred catheter. It will also be appreciated that, even when the catheter is pulled or twisted to such an extent that the outer sleeve does move slightly in respect to the adjacent body tissue, the resulting damage to those tissues will be significantly less than would generally be the case for prior art catheters. This is because the sleeve is very soft and compliant in response to the cushioning effect of the cushioning substance or lubricating gel in the sleeve cavity, and is therefore cushioned from what would be generally be a harsher, more rigid surface of the prior art catheters.

It will be appreciated from a further review of the present invention that the methods of the present invention provide great advantages over the prior art methods of making catheters which generally employ significant amounts of hand labor. These and various other advantages and features of novelty which characterize the present invention are pointed out with particularity in the claims annexed hereto and forming a part hereof. However, for a better understanding of the present invention, its advantages and other objects obtained by its use, reference should be made to the drawings, which form a further part hereof, and to the accompanying descriptive matter, in which there is illustrated and described preferred embodiments of the present invention.

BRIEF DESCRIPTION OF THE DRAWINGS

In the drawings, in which like reference numerals indicate corresponding parts throughout the several views, FIG. 1 is a transverse schematic view of an extruded tube in partial cross-section;

FIG. 2 is a transverse schematic view of an intermediate tube formed from the extruded tube shown in FIG. 1;

FIG. 3 is a schematic view of a portion of a rack or pallet used to retain a plurality of intermediate tubes during a series of steps designed to provide the tubes with overcoat layers of a polymeric bonding composition, wherein a single intermediate tube is shown secured to a single support rod and following a first dipping step wherein a portion of the outer surface of the intermediate tube is coating with a lubricating material;

FIG. 4 is a transverse schematic view of an intermediate tube similar to that shown in FIGS. 2 and 3, but following a second dipping step wherein the coating of lubricating material on the outer surface of the intermediate tube has been partially removed;

FIG. 5 is a transverse sectional schematic view of an intermediate tube similar to that shown in FIG. 4 following a subsequent dipping step or steps in which an overcoat layer is formed over the outer surface thereof;

FIG. 6 is a transverse sectional schematic view of an elongated catheter in accordance with the present invention;

FIG. 7 is a transverse schematic view of an extruded double lumen tube in partial cross-section;

FIG. 8 is a cross-sectional view of the extruded double lumen tube as seen from the line 8—8 of FIG. 7;

FIG. 9 is a transverse schematic view of the tube shown in FIG. 7 after an opening is punched in the outer surface;

FIG. 10 is a cross-sectional view of the tube as shown from the line 10—10 of FIG. 9;

FIG. 11 is a transverse schematic view of the double lumen tube shown in FIG. 9 after a portion of the first lumen has been filled with a polymeric bonding composition;

FIG. 12 is a cross-sectional view of the tube as seen from the line 12—12 of FIG. 11;

FIG. 13 is a transverse schematic view of the double lumen tube shown in FIG. 11 after a tip is affixed to a distal end of the tube;

FIG. 14 is a schematic view of a portion of a rack or pallet used to retain a plurality of tubes during a series of steps designed to provide the tube with an overcoat layer of a polymeric bonding composition;

FIG. 15 is a transverse schematic view of an intermediate tube similar to the tube shown in FIG. 13 at an intermediate stage of manufacture following to the first of a series of dipping steps;

FIG. 16 is a transverse schematic view of an intermediate tube similar to that shown in FIG. 15, but following a second dipping step wherein a coating of bond preventing lubricating agent on the outer surface has been partially removed;

FIG. 17 is a cross-sectional view of the intermediate tube of FIG. 16 as shown from the line 17—17;

FIG. 18 is a view of an intermediate tube similar to that shown in FIG. 16, but after a subsequent dipping step or steps;

FIG. 19 is a view of an intermediate tube similar to that shown in FIG. 18, but after yet another dipping step or steps;

FIG. 20 is a cross-sectional view of the balloon catheter shown in FIG. 19 from the line 20—20;

FIG. 21 is a transverse schematic view of a portion of a balloon catheter formed from the intermediate tube shown in FIG. 19, following a further dipping step to create an overcoat layer;

FIG. 22 is a perspective view of a portion of a balloon catheter similar to that shown in FIG. 21, but wherein the balloon catheter has been severed through the sleeve cavity and the remaining portion of the sleeve has been twisted to demonstrate its independence of the outer surface of the extruded double lumen tube used to make the balloon catheter;

FIG. 23 is a transverse schematic view of a balloon catheter similar to that shown in FIG. 21, but including an end piece and showing a sectional view of a portion of the catheter wherein the balloon portion of the catheter is expanded;

FIG. 24 is a cross-sectional view of an alternate embodiment of the balloon catheter shown in FIG. 23 as that embodiment would be seen from a line similar to the line 24—24 of FIG. 23, were FIG. 23 to show that embodiment;

FIG. 25 is a transverse schematic view similar to that shown in FIG. 23, but showing another alternate embodiment of a balloon catheter made in accordance with the present invention and including a plurality of first lumen access openings;

DETAILED DESCRIPTION OF THE PREFERRED EMBODIMENTS

Figure 26:
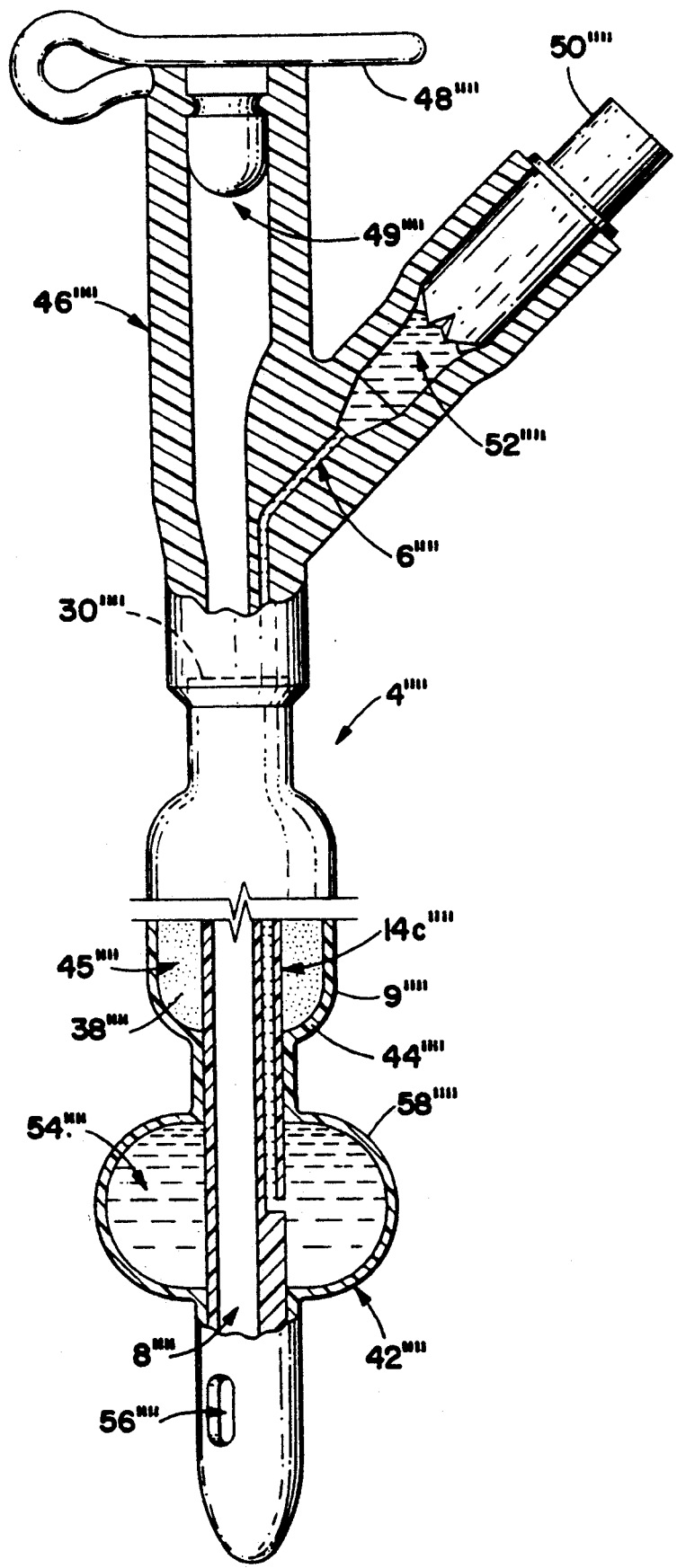
FIG. 26 is a transverse schematic view of yet another embodiment of the present invention similar to that shown in FIG. 23.

Referring now to the drawings, and specifically to FIGS. 1-6, the present invention provides an elongated catheter 5 (see FIG. 6) having an interior surface 7 and an exterior surface 9. The interior surface 7 defines a lumen 8. The elongated catheter 5 is preferably made from a tube 2 (see FIG. 1) which is eventually coated with an overcoat layer 42 of a resilient polymeric material which binds to an outer surface 14 of the tube 2 unless the bonding of the polymeric material is prevented by other materials or means on the outer surface 14.

The overcoat layer 42 of the elongated catheter 5 in accordance with the present invention, includes a sleeve 44 which encircles a sleeve cavity 45 which contains lubricating material 38. The lubricating material or substance 38 is effective to permit the sleeve 44 to slide along the outer surface 14 of the tube 2 proximate the sleeve 44 while in lubricated contact with the outer surface 14. When applied in sufficient thicknesses, the lubricating material serves to separate the soft outer sleeve 44 from the tube 2, such that the outer sleeve 44 provides a soft, cushioned, compliant exterior surface which can adapt and conform under slight pressures to the shape of the passageway in which it is inserted or residing. Depending on the catheter application and/or type, the amount of the lubricating substance 38 and the sleeve cavity 45 can be minimized to provide for only a limited increase in the outer diameter of the catheter proximate the outer sleeve 44. In other cases, a soft cushioned, compliant sleeve which can adapt its shape is desirable. In these embodiments, there is a relatively thick coating of lubricant material 38 in the sleeve cavity 45 which will give the sleeve 44 a balloon-like feel and appearance in the exterior surface proximate the sleeve 44. The elongated catheter 5 is preferably made of a flexible elastomeric material such as latex, silicone rubber or the like, most preferably silicone rubber. The lubricating material or substance 38 is preferably any biocompatible lubricating substance which is effective to permit respective polymeric surfaces to slide with respect to one another when in lubricated contact therewith. Preferably, the lubricating substance 38 is a hydrophobic oil or other petroleum based product or a water-soluble soap, detergent, gel or the like, either of which is effective to lubricate polymeric surfaces and to generally prevent bonding thereto by other polymeric substances when coated thereby. In a preferred embodiment, the lubricating substance 38 is petrolatum.

The first step in making an elongated catheter 5 in accordance with the method of the present invention is to provide a tube 2 having an outer surface 14 and an inner surface 7 defining a first lumen 8. The distal end 16 of the tube 2 is preferably inserted into a molding apparatus (not shown) designed to mould a tip 20 on the distal end 16 of the tube 2 to form the intermediate tube 3 (see FIG. 2). In a preferred process of the present invention, the intermediate tube 3 is then secured on a support rod 26 of a rack or pellet 24 which preferably includes a plurality of support rods 26. Preferably, a plurality of intermediate tubes 3 are secured on the plurality of support rods prior to subjecting the intermediate tubes 3 secured on the support rods 26 to a series of dipping steps in the preferred process.

After the intermediate tube 3 is formed from the initial tube 2, the outer surface is coated from the lowest portion of the tip 20 up to a location on the outer surface 14 designated by the dashed line A, as shown in FIG. 3, with the lubricating substance. Subsequently, the lubricating substance coating the outer surface 14 of the tube below a location proximate the dashed line designated B, as shown in FIGS. 3 and 4, is stripped from the outer surface 14 and the tip 20. The intermediate tube 3 is then coated with a resilient polymeric bonding composition which forms the overcoat layer 42. The overcoat layer 42 bonds to the tip 20 and a portion of the outer surface 14a below the dash line designated B, and to a portion of the outer surface 14b above the line designated A. In the area proximate to a portion of the outer surface 14c between the dash lines designated A and B, respectively, which remains coated with lubricating material 38, the overcoat layer 42 forms a sleeve 44 which encircles the lubricating material 38 coating the portion of the outer surface 14a between the dash lines designated A and B, which cooperates with the sleeve 44 to define the sleeve cavity 45 in which the lubricating material 38 proximate the sleeve 44 is contained. After the overcoat layer 42 is formed upon the intermediate tube 3, a pair of fluid conduit openings 56 are preferably created, most preferably punched, to permit fluid to pass into or out of the lumen 8 proximate the distal end 16. It will be appreciated that, although the overcoat layer 42 and the wall 11 of the tube 2 are shown in FIG. 6 to be separate elements, when made of identical polymeric materials, as is the case with the most preferred embodiments of the present invention which are made of silicone rubber, the wall 11 and the overcoat layer 42 will be bonded together where they interface with one another so that it is virtually impossible to distinguish between the two and so that there is no part line in spite of the fact that a part line is shown in FIGS. 5 and 6. In the preferred embodiments, where these elements are joined together, it will be appreciated that they form an integral membrane or wall.

The specific procedures used to form the present elongated catheter 5 will include steps similar to the steps used for similar purposes as described hereinbelow.

Referring now to FIGS. 7 and 8, the first step in making a balloon catheter in accordance with the present invention is providing a double lumen tube 2', which is preferably extruded and made of silicone rubber. It will be appreciated, however, that the double lumen tube 2' can be made by any known process which yields a double lumen tube 2'. It will be further appreciated that the tube 2' can be made of any resilient polymeric material, preferably a biocompatible polymeric material which can be inserted into a human body cavity. The double lumen tube 2' includes a smaller capillary lumen 6' and a larger fluid conduit lumen 8'.

Referring now also to FIGS. 9 and 10, after the double lumen tube 2' is cut to a desired size, a capillary lumen access opening 12' is created in an outer surface 14' of the double lumen tube 2'. The capillary lumen access opening 12' communicates with the capillary lumen 6'.

Referring now also to FIGS. 11-13, an intermediate tube 3' is subsequently prepared from the double lumen tube 2' shown in FIG. 9. In the first step of this process, a measured amount of a polymeric bonding composition, preferably silicone rubber or another suitable polymeric bonding material, is injected into the capillary lumen 6' from the distal end 16' of the double lumen tube 2', so that the capillary lumen 6' is filled with a polymeric fill material 18' up to a point just below the capillary lumen access opening 12'. A tip 20', preferably a rounded silicone rubber tip, is then affixed to the distal end 16' of the tube 2' to complete the formation of the intermediate tube 3' shown in FIG. 13. In a preferred method, the distal end 16' of the tube 2' is inserted into a molding apparatus (not shown) designed to mold a tip 20' on the end of the tube 2'.

Referring now also to FIGS. 14-21 and 28, a preferred process of the present invention involves securing a plurality of intermediate tubes 3', like the intermediate tube 3' shown in FIG. 13, to a rack or pallet 24'. The rack or pallet 24' will include a plurality of support rods 26', each equipped with a retaining clip 28'. The intermediate tubes 3' are secured on the support rods 26' by engaging individual support rods 26' in the larger of the two lumens 8', called the fluid conduit lumen 8', and sliding the intermediate tubes 3' up over the support rods 26' until the proximal ends 30' of the intermediate tubes 3' abut against the base of the retaining clips 28' or, preferably, the tip 20' of each of the intermediate tubes 3' fits snugly against the distal tip 26a' of each of the support rods 26', as shown in FIGS. 15 and 16. Although not shown, it is believed that the intermediate tubes 3' can be secured on the support rods 26' without the aid of the retaining clips 28'. This is because the preferred extruded double lumen tubes 2' used to make the intermediate tubes 3' generally have a slight bend in one direction or another when they are hung. This results in a slight bend in the intermediate tubes 3' that permits the intermediate tube 3' to be secured on a support rod 26' without the aid of a clip 28'. Because of the nature of the polymeric materials generally used to make the intermediate tubes 3', they also have a tendency to cling to other surfaces and to offer resistance to movement of a surface along a surface of this material as do most polymeric tubes including those tubes 2 described hereinabove.

When the intermediate tubes 3' have been secured on the support rods 26', the pallet 24' can be transferred from place to place, and the intermediate tubes 3' on the pallet 24' can be dipped in a series of baths (see FIG. 26) prepared to accomplish a series of process steps. In the preferred method of the present invention, the intermediate tube 3' is made entirely of silicone rubber and is secured upon a support rod 26' made of spring steel. The tip 20' and the fill material 18' of the intermediate tube 3' shown in FIG. 13 are made of the same material (silicone rubber) as the double lumen tube 2'. Therefore, the tip 20' and the fill material 18' preferably form integral portions of the intermediate tube 3', which is shown in FIGS. 15-21.

The first step in the automated coating or dipping process of forming the resilient sleeve 44' and the balloon portion 32' of the balloon catheter 4' (shown in FIG. 21), after the intermediate tubes 3' are secured to the pallet 24', is to coat the intermediate tubes 3' with a bond preventing lubricating agent or substance 38', preferably a removable bond preventing lubricating agent. Preferably this is accomplished by dipping each of the tubes 3' on the pallet 24, simultaneously into a first dip tank 33 containing a bath 33a of a removable bond, preventing agent preferably a material which forms a semi-solid film on surfaces when cooled on contact followed by an opportunity for drying. Examples of such materials include petroleum jelly or petrolatum, other oil base substances which form a semi-solid upon cooling to room temperature, liquid soaps which dry to form a semi-solid, aqueous soap or detergent solutions, aqueous or oil based film forming solids emulsions, and the like. In one embodiment described herein, hot petrolatum is used, and in another, a liquid soap is used, preferably Liquid Ivory Soap from Proctor & Gamble, Cincinnati, Ohio.

When the intermediate tubes 3' are removed from this first bath 33a of removable bond preventing lubricating agent 38', the agent or substance 38' adheres to the outer surface 14' of the intermediate tube 3', and occupy the capillary lumen access opening 12' and the capillary lumen 6'. In one embodiment the agent is petrolatum, which is heated to about 140°-160° F., preferably about 150° F. At these temperatures, the petrolatum will run up into the capillary lumen 6' through the capillary lumen access opening 12' with the assistance of the "capillary effect", which draws the fluid into the capillary lumen 6' to the level of the petrolatum in the first tank 33. As the intermediate tubes 3' are withdrawn from the hot petrolatum, petrolatum on each tube cools and solidifies to form a semi-solid coating 38' on the outer surface 14' and a semi-solid filling (not shown) in the capillary lumen 6' and the capillary lumen access opening 12' which cooperate to plug the capillary lumen access opening 12'. In an alternate embodiment, the bond preventing agent in the first tank 33 is liquid soap at room temperature (about 62°-74° F.). When the tubes 3 are withdrawn from the first dip tank 33, the liquid soap forms a semi-solid just as the hot petrolatum did as it cooled.

In the preferred method of the present invention, the intermediate tubes 3' are coated when they are dipped in a first bath 33a which contains petrolatum which is maintained at a temperature effective to permit the petrolatum to coat the outer surface 14 of the tube while limiting the degree to which the petrolatum runs into the smaller lumen 6'. The petrolatum will run into the first lumen access opening 12', but, preferably, will not run very far into the smaller lumen 6'. The temperature of the petrolatum in the first tank 33 is preferably maintained at about 40°–80°, more preferably about 50°–70°, even more preferably about 55°–65°, and most preferably about 60° C. for this purpose. As shown in FIG. 15, the intermediate tube 3' is coated with the bond preventing lubricating agent 38' up to a location on the surface 14' of the intermediate tube 3' proximate the dashed line A shown in FIG. 15 by dipping the intermediate tube 3' into the first dip tank 33 up to that point.

Following this step, the outer surface 14' of the intermediate tube 3' is stripped of the bond preventing lubricating agent 38' up to a location proximate the dashed line designated B in FIGS. 15 and 16. This is preferably accomplished by one or more dipping steps in accordance with the methods for stripping particular lubricating agents as described hereinbelow. The intermediate tube is then preferably coated as shown in FIG. 16 between the locations proximate the dashed lines A and B. The intermediate tube 3" shown in FIG. 16 is then dipped in a subsequent dip tank holding a second bond preventing agent. In this step the liquid soap can be preferred, although petrolatum and other agents will also work. During this step, the intermediate tube 3' shown in FIG. 16 is dipped into the tank up to a point on the outer surface 14' of the intermediate tube 3' proximate the dashed line C so as to coat the portion of the intermediate tube 3' from the lowest portion of the tip 20' up to the location proximate the dashed line designated C. In preferred embodiments of the present invention, any of the bond preventing lubricating agents enumerated above may be used. Preferably, however, the bond preventing lubricating agent is hot petrolatum heated to about 130°–150° F., preferably about 140° F. (about 60° C.), or liquid soap at room temperature (about 62°–74° F.). When the intermediate tubes 3' are withdrawn from the hot petrolatum, petrolatum will cool and solidify to form a semi-solid coat 39 on the outer surface 14' and a semi-solid filling 34' in the capillary lumen 6' and the capillary lumen access opening 12' which cooperate to plug the capillary lumen access opening 12' as shown in FIG. 18. As stated above, soap at room temperature will provide the same function as the petrolatum. The intermediate tube is then subjected to a further dipping step wherein the intermediate tube shown in FIG. 18 is dipped in one or more dip tanks so as to strip the coating of bond preventing agent 39 from the portion of the intermediate tube 3' below a location on the outer surface 14' proximate the dashed line designated D in FIGS. 18 and 19 so as to strip the tube of bond preventing agent below that location.

After the intermediate tubes 3' are coated in this manner and the capillary lumen access openings 12' are plugged with bond preventing agent 40, the tubes 3' are then dipped in a series of dip tanks (see FIG. 26) provided to coat the intermediate tube 3' with a polymeric bonding composition, preferably silicone rubber, in a step or steps provided to form the overcoat layer 42', including both the resilient sleeve 44' and balloon portion 58' of the balloon catheter 5' shown in FIG. 21. In the preferred methods, the intermediate tube 3' is dipped in silicone rubber in two or more successive dipping steps so that the resulting overcoat layer 42' includes underlying and an overlying layers (not shown), which form an integral part of the balloon catheter 5' and are bonded together, and to the outer surface 14' in the portions thereof, 14a', 14b' and 14d', which are located below the dashed line designated D, between the dashed lines designated B and C, and above the dashed line designated A, respectively. The portion 14d' above line A was not coated prior to the final dipping steps designed to provide the overcoat layer 42', and the portion 14a' below line D was stripped of its coating prior to those steps.

In subsequent steps, the proximal end 30' of the balloon catheter 5' is secured to an end piece 46' to form a completed Foley catheter 4' (shown in FIG. 23). The end piece 46' can include a cap 48' for closing a proximal end access opening 49' to the fluid conduit lumen 8' and can be equipped with a luer valve 50' for engagement in and closure of the proximal capillary lumen access upper opening 52' communicating with the capillary lumen 6'. Prior to the attachment of the end piece 46' to the sleeved balloon catheter 5' to form the completed sleeved Foley catheter 4', the sleeved balloon catheter 5' is preferably allowed to air dry to permit solvents in the overcoat layer 42' to evaporate and is subsequently cured at an elevated temperature. Care is taken to keep the curing temperature below the boiling temperatures of the solvent so as to prevent unsightly bubbling of the solvent within the overcoat layer 42'. Because the overcoat layer 42' is preferably made of the same polymeric bonding composition, even though it may be created in a plurality of dipping steps, it is represented in FIGS. 21–25 as a single overcoat layer 42'. It will be appreciated, however, that this single overcoat layer 42' may or may not represent an integral layer formed in a series of dipping steps wherein there may be any number of underlying or overlying layers. The completed Foley catheter 4' also includes a fluid conduit access opening 56' in an exterior surface 62' of the completed Foley catheter 4'. The fluid conduit access opening 56' communicates with the fluid conduit lumen 8'.

Referring now also to FIG. 22, the independence and stretchability of the resilient sleeve 44' is illustrated. The resilient sleeve 44', not only has a narrower thickness than the inner wall 21' of the catheter 5', but it is also more flexible, more stretchable, and preferably less rigid than the inner wall 21'. The lubricating substance 38' contained in the sleeve cavity 45' permits the sleeve 44' to slide along and in respect to the outer surface 14' while in lubricated contact therewith and when stretched independently thereof. As illustrated in FIG. 22, the resilient sleeve 44' can be twisted in respect to the inner wall 21' without twisting the inner wall 21' or the respective lumens, 6' and 8'. The resilient sleeve 44' can also be stretched without stretching the inner wall 21' of the catheter 5'. As stated hereinabove, this enables the resilient sleeve 44' to stay in relative contact with or in adherence to adjacent body tissues (not shown) with which the resilient sleeve 44' is in contact with even when the remaining portions of the sleeved balloon catheter 5', such as the inner wall 21', are forced to move in response to forces impacting on the catheter 5' at other points along its length. The resilient sleeve 44 can also change from its initial circumferential shape to a more ribbon-like oval shape in order to match the shape or contour of the passageway in which it resides. The volume of the sleeve cavity 45 will preferably increase the outside diameter of the catheter proximate the sleeve portion at least about 5%, preferably about 10%, more preferably about 20%, even more preferably about 25%, even more preferably about 35%, and even more preferably about 50%. It is conceivable that applications will also be found where the thickness of the lubricating substance in the sleeve cavity 45 is increased so as to increase the volume of the sleeve cavity such that the outside diameter of the catheter proximate the sleeve 44 will be increased from about 50 to 100, or 50 to 200% or more depending on the particular application. The important factor is that the sleeve be soft and compliant so that it can conform to the shape of the particular passageway in which it resides and, at the same time fill the passageway so as to limit the passage of fluids along either the wall of the passageway or the exterior surface of the catheter, and at the same time, to allow the inner conduit portion of the catheter move relatively independently of the exterior surface of the sleeve 44 of the catheter.

In preferred methods in accordance with the present invention, the end piece 46' is made by a process of injection molding. Preferably, the proximal end 30' of the sleeved balloon catheter 5' is inserted into an injection molding apparatus (not shown) after the overcoat layer 42' has been cured. However, it will be appreciated that the end piece 46' can be added to the intermediate tube 3' prior to the initiation of the dipping process. A polymeric bonding composition, preferably silicone rubber, is injected into the mold (not shown) and the end piece 46' is molded onto the proximal end 30' of the balloon catheter 5' to make the completed Foley catheter 4' shown in FIG. 23. Following further drying, curing steps, where deemed necessary given the type of polymeric bonding composition or compositions used to make the completed Foley catheter 4', the completed catheter 4' is tested to see if it is functional and if it has any leaks. This testing can be done before or after the fluid conduit access opening 56' is created in the exterior surface 62' to communicate with the fluid conduit lumen 8'.

In order to test the integrity of the completed catheter 4', prior to engaging the plug 50' in the proximal capillary lumen access opening 52' in the end piece 46', the proximal capillary lumen access opening 52' is slipped over a hot water nozzle (not shown), and a measured amount of a hot aqueous solution, preferably water or water containing a trace of surfactant, at a temperature of between about 120°-160° F., preferably about 140° F., is pumped into the capillary lumen 6' from a standard hot water heater (not shown) by a commercially available water pump (not shown) such that the balloon portion 58' is expanded. It will be appreciated that higher or lower temperatures can be used so long as the desired coating properties for the particular application desired can be obtained. The balloon portion 58' of the overcoat layer 42' is the portion of the overcoat layer 42' which is not bonded to the outer surface 14' of the intermediate tube 3' proximate a balloon cavity 54'. The balloon portion 58' of the overcoat layer 42' cooperates with the portion 14c' of the outer surface 14' which remained coated with the bond preventing agent prior to the step of dipping the intermediate tube 3' in the polymeric bonding composition, to define the balloon cavity 54'. The balloon cavity 54' communicates with the capillary lumen 6' via the capillary lumen access opening 12'. When the hot water solution is pumped or injected into the capillary access lumen 6' to test the completed catheter 4' and the balloon portion 58', the balloon portion 58' and the balloon cavity 54' are expanded. If there is a significant lack of integrity in the balloon portion 58' it will be exposed when the water is introduced in this manner. In addition to testing the balloon portion 58', the water solution will also remove the remaining bond preventing agent in the balloon lumen 54' and the capillary lumen 6' when it is removed. Although some of the bond preventing agent may come out of the capillary lumen 6' via the proximal capillary lumen access opening 52' during the step of curing the overcoat layer 42', the hot aqueous solution is generally believed to remove most of the bond preventing agent, although a residue may remain.

Following the preliminary test, which relies on a visual observation to determine whether there is any lack of integrity, a further test is used to obtain further assurance that there are no leaks in the balloon portion 58. This further test is accomplished by engaging the proximal capillary lumen accessing opening 52' to the nozzle of a commercially available leak tester (not shown). One such device is a Model No. 6510 Caps Tester from Caps Himmelstein (Hoffman Estates, Ill. 60195). Once the completed catheter 4' is tightly secured over the nozzle, an electrical switch, such as a hand switch or, preferably, a foot pedal, is used to release a measured blast of air into the capillary lumen 6'. When the air is introduced into the capillary lumen 6' it also enters the balloon cavity 54' via the capillary lumen access opening 12' and inflates the balloon portion 58' and, thereby, expands the balloon cavity 54'. The leak tester is designed to sense any loss of pressure once the balloon portion 58' is inflated, and will given an indication, therefore, if there are any measurable leaks. After this test is completed, the completed sleeved Foley catheters 4' that have passed all tests, are then packaged, preferably in a material which breathes such as Tyvek TM (from DuPont), and boxed. The boxes are then sterilized with ETO (Ethylene Oxide) and then stored for shipment.

In a preferred embodiment of the present invention, the extruded double lumen tube 2' used to make the intermediate tube 3' is a tube (not shown) which has a series of generally parallel undulations running generally parallel with the longitudinal axis of the tube (see FIG. 24). When such a tube is used, a sleeved Foley catheter 4" having a ribbed inner surface 60 on the balloon portion 58" of the completed Foley catheter 4" will result because the bond preventing coating 40' (not shown) on the intermediate tube 3" will reciprocate the undulations in the outer surface 14" of the intermediate tube 3". Therefore, when the balloon portion 58" of the overcoat layer is created, the inner surface 60 will have ribs 59 which reciprocate the undulations in the bond preventing coating material 40' coating the coated portion 14c" of the outer surface 14".

Referring now also to FIG. 25' another embodiment of the present invention provides a completed sleeved Foley catheter 4" which has a plurality of capillary openings 12"' that permit greater access to the balloon lumen 54"' from the capillary lumen 6"' and vice versa. This can be very important when wishing to ensure that the access to the capillary lumen 6"' from the balloon lumen 54"' is not blocked once the balloon portion 58"' of the overcoat layer 42"' is expanded.

In the Applicants' use of the preferred methods of the present invention, balloon and sleeve fabrication is almost completely automated. Entire sets of sleeved balloon catheters 5' are manufactured simultaneously. The preferred pallet 24 has 400 spring steel support rods 26 attached to a pallet in 20 rows of 20 rods, wherein each of the rods 26 is about 1 inch from each adjacent rod. Single and double lumen tubing (not shown) is preferably made by extrusion processes known to those of skill in the art. The tubes 2 and 2' are cut to length as the tubing leaves the extruder (not shown). An opening 12' is created in the outer surface 14' of the double lumen tubes 2', preferably with a hollow drill bit or drill tube (not shown), so as to communicate with the capillary lumen 6' in those tubes 2'. The distal portion 6a' of the capillary lumen 6', located between the distal end 16' of the tube 2' and the capillary lumen access opening 12', is then injected with a measured amount of a polymeric bonding composition, preferably silicone rubber, so that the distal portion 6a' is filled and sealed. A rounded tip 20' is then formed at the distal end 16' of the double lumen tube 2', preferably by inserting the tube 2' in a molding device (not shown).

Referring now also to FIG. 26' another preferred embodiment of the present invention is illustrated in this embodiment of the present invention as sleeved Foley catheter 4''''. It is very similar to the catheter shown in FIG. 23 except that the space between the balloon cavity 54'''' and the sleeve cavity 45'''' has been decreased so that it will accommodate the urethral sphincter of the bladder. In addition, the volume of the lubricating substance 38'''' in the sleeve cavity 45'''' is significantly more than that shown in FIG. 23. This is accomplished by increasing the thickness of the lubricating substance 38 which is coated onto the intermediate tube carrying the manufacturing process. The increase in the thickness of the lubricating substance 38'''' allows the sleeved Foley catheter 4'''' to provide a very soft, "cushy", conforming exterior surface 9'''' proximate the sleeve 44'''' which can accommodate variations in the surfaces with which the catheter 4'''' comes into contact.

Figure 27:
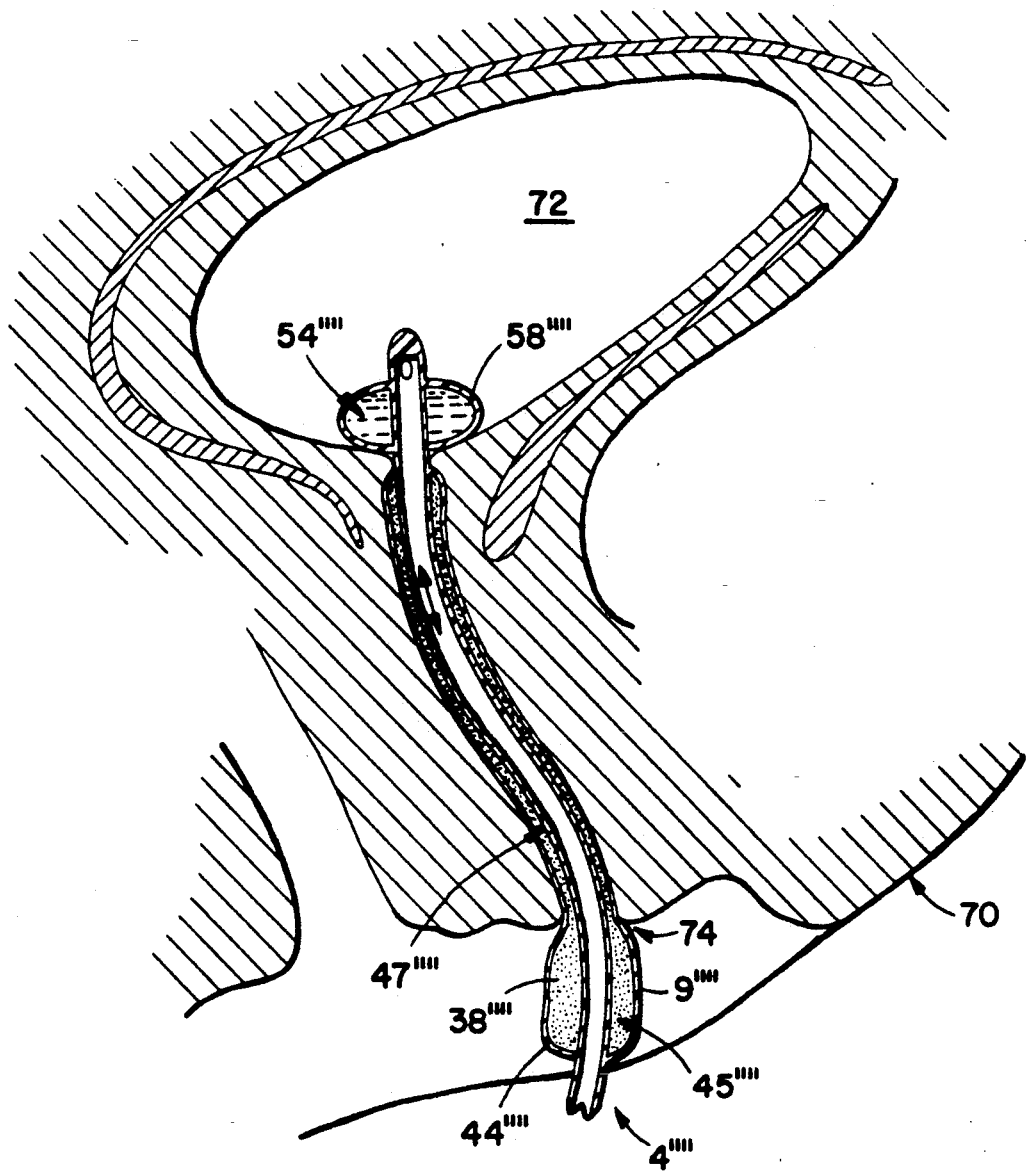
FIG. 27 is a transverse schematic sectional view showing a portion of the catheter shown in FIG. 26 when inserted in a urethral tract.
Figure 28:
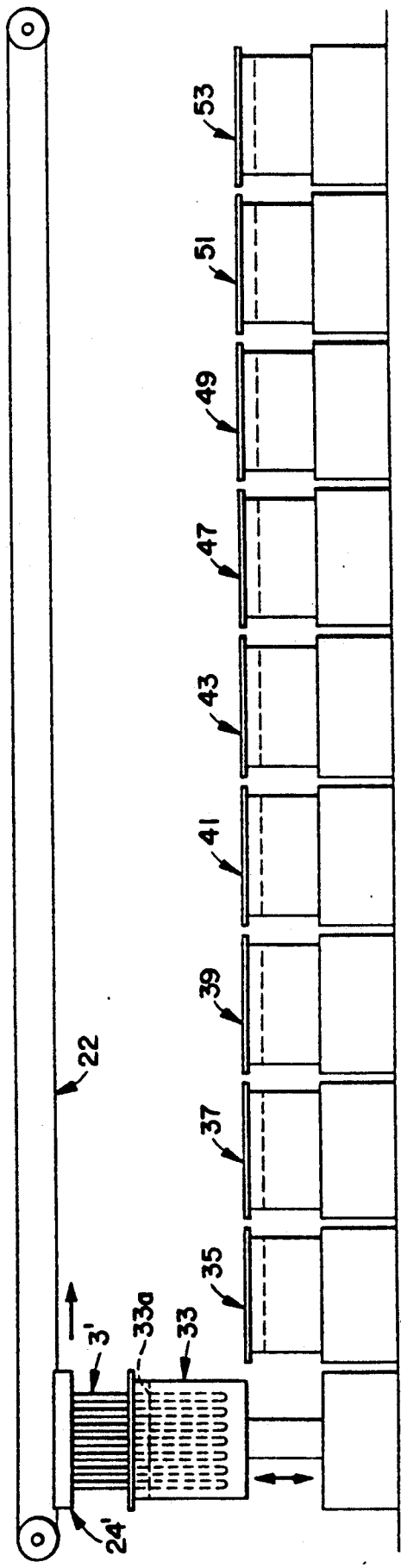
FIG. 28 is a schematic illustration of apparatus used to automate the production of catheters in accordance with the present invention.

Referring now also to FIG. 27, the sleeved Foley catheter 4'''' shown in FIG. 26 is shown when inserted into a urethral tract 74 of a woman 70 the balloon portion 58'''' of the catheter 4'''' resides within the bladder 72 of the woman 70. The balloon portion 58'''' is expanded to retain the catheter 4'''' in the urethral tract 74. The harsh volume of lubricating substance 38'''' in the sleeve cavity 45'''' is shown to provide a exterior surface 9'''' proximate the sleeve 44'''' which conforms to the wall of the urethral tract 74. The lubricating substance 38'''' also allows the inner wall 21'''' or conduit portion 21'''' of the catheter 4'''' to move back and forth within the urethral tract 74'''' to a limited degree without disrupting the interface between the exterior surface 9'''' proximate the sleeve 44'''' and the adjacent body tissues of the urethral tract 74. This allows the catheter 4'''' to move in all directions to a limited degree without disrupting this interface, thereby increasing the comfort of the patient in which the catheter 4'''' resides.

In the most preferred embodiments of the present method, 400 of the intermediate tubes 3' are then mounted vertically on rigid spring steel support rods 26' on a pallet 24' in the manner previously described. The pallet 24' is then moved via a transporting mechanism 22 (see FIG. 28) over a series of dip tanks as follows in the following example which will further disclose preferred elements of the present invention.

EXAMPLE I (A) The pallet 24' is stopped over a first tank 33, which contains white USP petrolatum heated to about 60° C. (about 140° F.). The tank is raised so as to immerse the intermediate tubes 3' into the petrolatum to such a depth that the petrolatum reaches the proximal end of the desired sleeve location. The dip tank 33 is then lowered and a portion of the outer surface 14' of the intermediate tubes 3' are coated with petrolatum. This portion extends from the general point at which the proximal end of the resilient sleeve 44' will begin, to the distal end 20a' of the tip 20' of the intermediate tube 3'. This step is repeated when it is desireable to build up the thickness of the lubricating substance and the resulting volume of the sleeve cavity so as to increase the resulting increase in the outside diameter of the particular catheter over the circumferential diameter of the conduit portion or tube 2 or 2' of this present invention.

(B) The pallet 24' is then automatically advanced and stopped over a second dip tank 35 which contains white USP petrolatum heated to about 120° C. (about 250° F.). The second dip tank 35 is raised so as to immerse the intermediate tubes 3' into the super-heated petrolatum so that the super-heated petrolatum comes into contact with the petrolatum coating 38' on outer surface 14' of the intermediate tube 3' from the prior dipping step up to a general location where a distal end of the resilient sleeve 44' will end. The second dip tank 35 is then lowered. This dipping step causes the coating of petrolatum from the prior dipping step to be largely removed from the portions 14a the outer surface 14' below a location where the distal end of the resilient sleeve 44' will be generally located (designated by dashed line B) to the distal end 20a' of the tip 20' of the intermediate tube 3'. Some residual petrolatum may remain on the outer surface 14' of the intermediate tube 3' in this area of the outer surface 14'. However, most of the petrolatum is removed.

(C) The pallet 24' is then automatically advanced and stopped over a third dip tank 37 containing mineral spirits heated to about 200° F. The third dip tank 37 is then raised so as to immerse the intermediate tubes 3' into the mineral spirits to the same depth as they were immersed in the super-heated petrolatum in the second dip tank 35. The tank 37 is then lowered and all but a trace amount of the petrolatum is removed from the outer surface 14 located generally below the dashed line B, which will eventually be proximate the sleeve 44'.

(D) The pallet 24' is then automatically advanced and stopped over a fourth dip tank 40 containing a volatile organic solvent such as toluene, trichloroethane or the like. The fourth tank 40 is then raised to immerse the intermediate catheters 3 to the same depth as previously immersed in the second and third tanks 35 and 37, thereby removing essentially all traces of the petrolatum from this portion of the outer surface 14'. The intermediate catheter tube 3' now has a band 38' of semi-solid petrolatum located around the axial circumference of the intermediate tube 3' in the location where the sleeve cavity 45' will be created.

(E) The pallet 24' is then stopped over a fifth, sixth, seventh and eighth dip tank, 41, 43, 47 and 49, respectively, where the steps enumerated in steps A, B, C, and D, respectively, are repeated with the following variation. When the pallet 24' is stopped over the fifth dip tank 41, the intermediate tubes 3' are immersed only up to a location proximate the dashed line designated C as shown in FIGS. 18 and 19. When the pallet 24' is subsequently stopped in series over dip tanks 43, 47 and 49, the intermediate tubes 3' on the pallet 24' are only immersed up to a location proximate the dashed line D as shown in FIGS. 18 and 19. Following these steps, the petrolatum is stripped from the portion 14a' of the outer surface 14' located below the location proximate the dashed line designated D. The petrolatum not only coats the portion 14c' of the outer surface 14' located in this area, but also fills a portion of the capillary lumen 6' and plugs the capillary lumen access opening 12', which will eventually be used to inflate the balloon portion 58' of the completed Foley catheter 4'.

(F) The pallet 24' is then lowered and automatically advanced to a ninth dip tank 51 containing a low-solids silicone rubber/solvent dispersion which is effective to minimize any disruption of the integrity of the petrolatum coatings 38' or 40' remaining on the intermediate tube 3' proximate the portions 14e and 14c of the outer surface 14' where the sleeve cavity 45' balloon cavity 54' will be created during subsequent dipping steps. The ninth tank 51 is then raised to immerse the intermediate tube 3' in the solution up to a location above the dashed line designated in A in FIG. 19. This step can be subsequently repeated at intervals, preferably allowing time for significant solvent evaporation, either in the same tank or in a subsequent tank containing a greater concentration of silicone rubber, until the overcoat layer 42 and the balloon portion 58 of the overcoat layer 42 have a desired balloon thickness. However, in the present embodiment, the tank 51 is lowered, the pallet 24' is advanced to a tenth dip tank 53 containing a silicone rubber dispersion having a higher silicone rubber concentration than the dispersion in the ninth dip tank 51, and the tubes 3' are completely immersed again. The preferred thickness over the overcoat layer 42', the resilient sleeve 44' and the balloon portion 58' is 17.5 thousandths of an inch (plus or minus 2.5 thousandths of an inch). Where subsequent silicone rubber dip tanks are provided, the concentration of silicone rubber in the subsequent tanks are preferably greater than the concentration of the silicone rubber in the ninth tank 51. It is also desirable to alter the silicone rubber used in a final coating to provide greater sheen and a smoother finish, however, the concentration and the solvent may be adjusted as deemed appropriate.

(G) The pallet 24' is then advanced through a drying area where solvents are allowed to evaporate, and then through a heat cure step, where the sleeved balloon catheters 5' formed by this process are cured at a temperature just below the boiling point of any solvent used in any of the silicone rubber dip dispersions. For toluene this temperature is about 200° F.

(H) After the heat cure, the sleeved balloon catheters 5' are allowed to cool and are then removed from the support rods 26'. The proximal ends 30' of each of the balloon catheters 4 is then inserted into an injection molding apparatus (not shown), which forms the end piece 46' of the completed sleeved Foley catheter 4'.

(I) The completed Foley catheters 5 are then finished by punching a fluid conduit access opening 56' in the exterior surface 62' such that it communicates with the fluid conduit lumen 8' in a location below or distal to the balloon portion 58' of the overcoat layer 42'.

(J) The completed Foley catheters 4' are then sent through the test sequence described hereinabove, during which the balloon portion 58' of each completed Foley catheter 4' is inflated and the petrolatum band 40' within the balloon cavity 54' is largely removed.

Figure 29A:
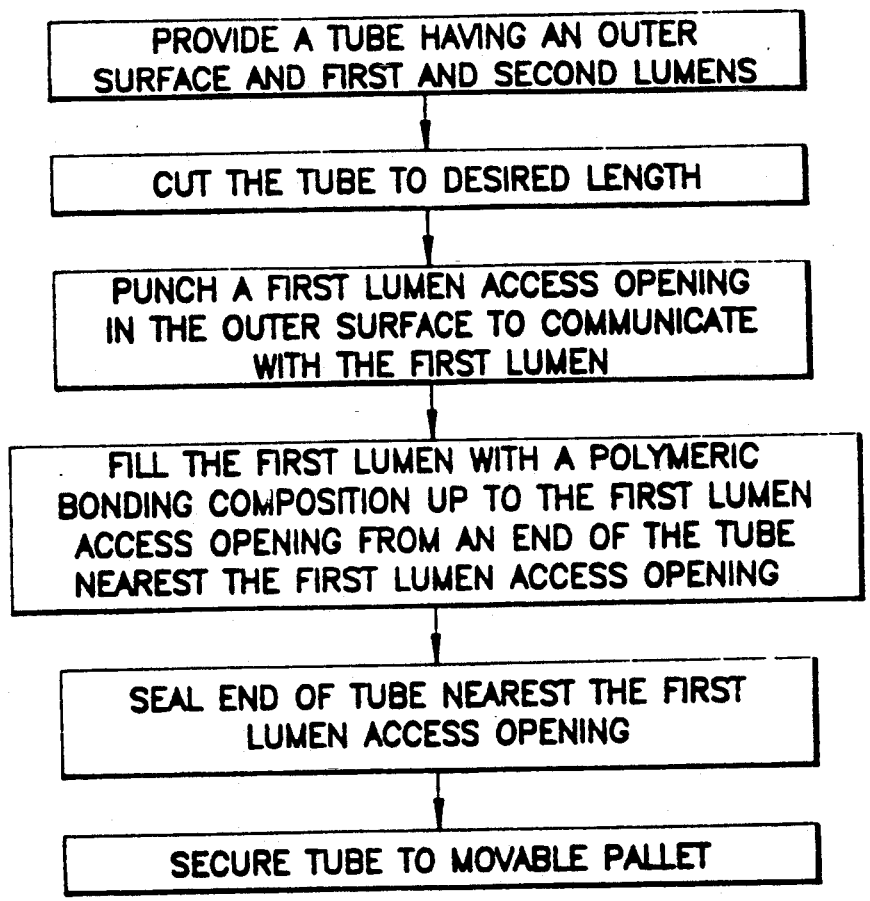
FIG. 29a, 29b and 29c are flow charts representing certain steps in methods in accordance with the present invention.
Figure 29B:
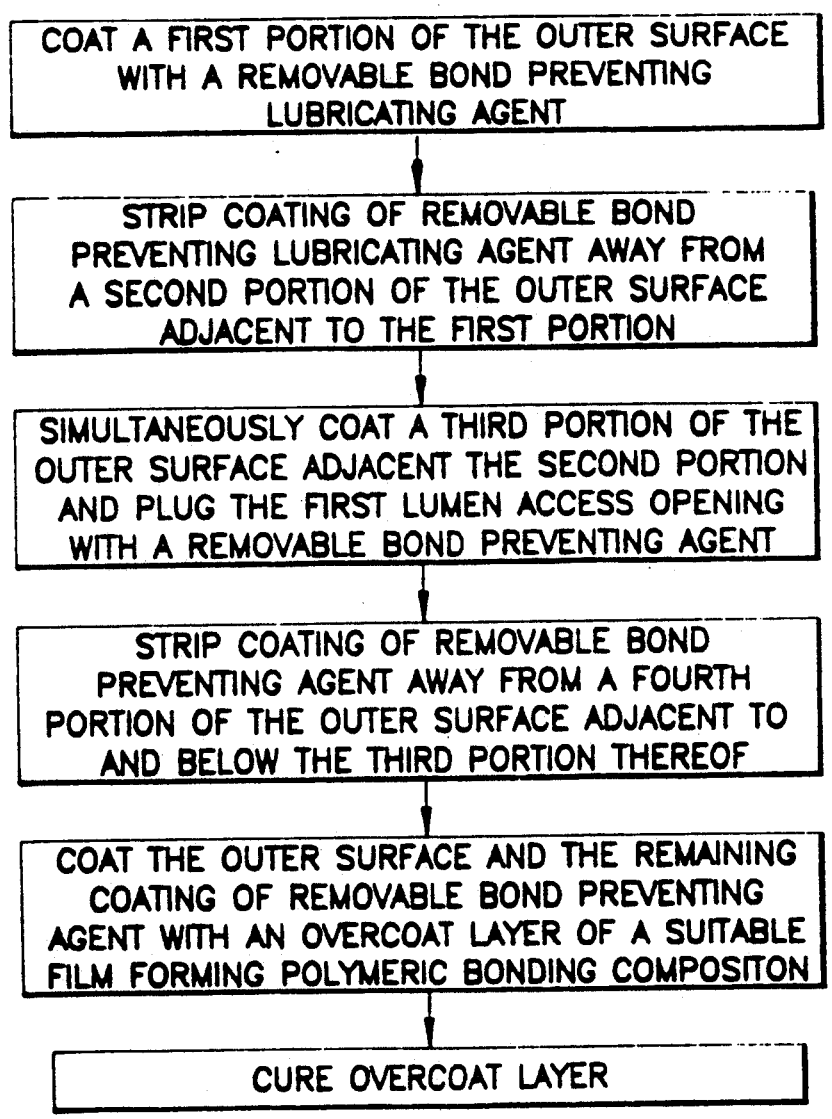
Figure 29C:
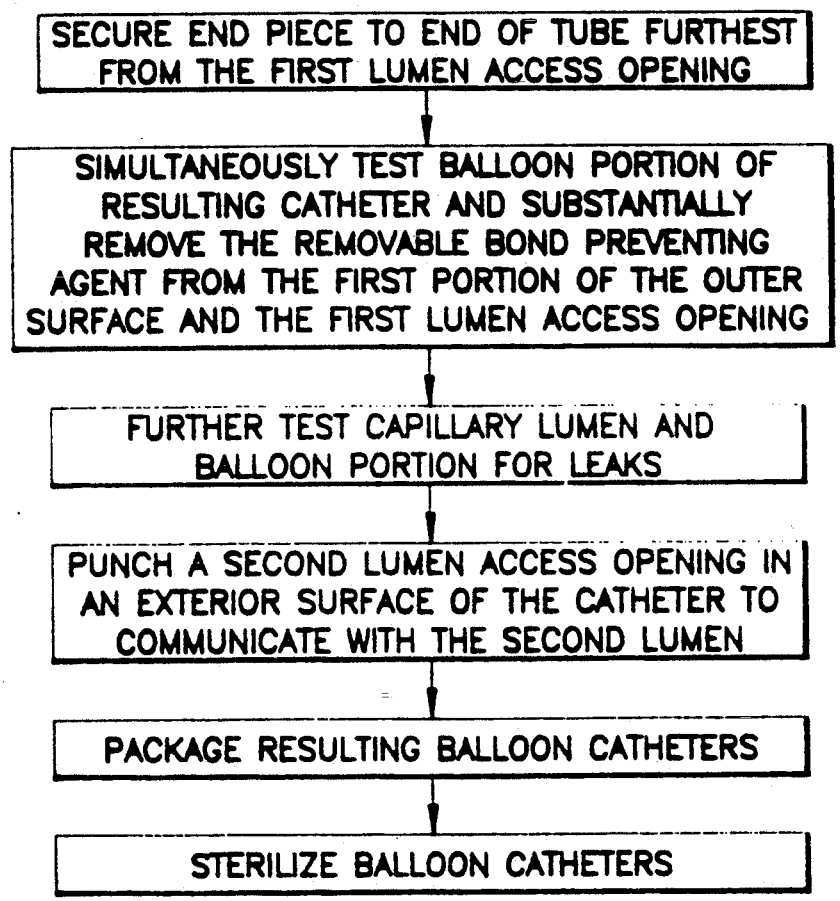
Figure 27:
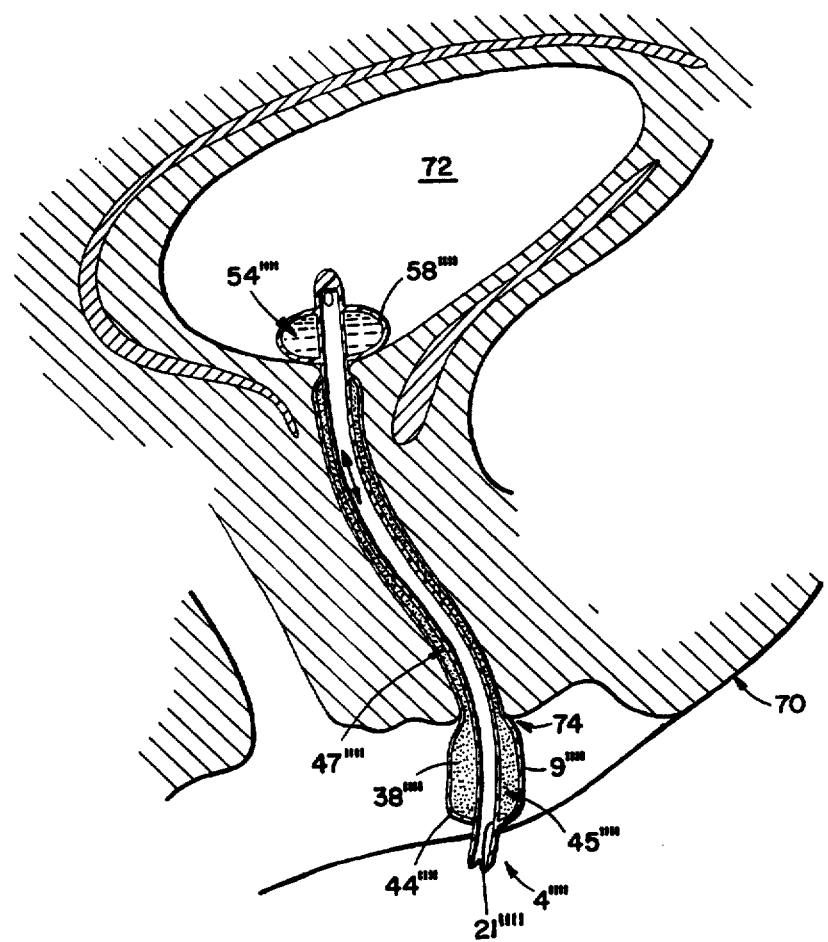

Referring now also to FIGS. 29a, 29b and 29c, the present invention provides a method of making sleeved Foley catheters 4' including the following steps:

(A) Providing a tube having an outer surface and first and second lumens;

(B) Cutting the tube to a desired length;

(C) Creating a first lumen access opening in the outer surface to communicate with the first lumen;

(D) Filling the first lumen with a polymeric bonding composition up to the first lumen access opening from an end nearest the first lumen access opening;

(E) Sealing the end of the tube nearest the first lumen access opening; and (F) Securing the tube to a movable pallet.

These steps are followed by the following steps:

(A) Coating a first portion of the outer surface and plugging the first lumen access opening with a removable bond preventing lubricating agent;

(B) Stripping the coating of removable bond preventing lubricating agent away from a second portion of the outer surface adjacent to the first portion;

(C) Simultaneously coating a third portion of the outer surface adjacent to the second portion thereof and plugging the first lumen access opening with a removable bond preventing agent;

(D) Stripping the coating of removable bond preventing agent away from a fourth portion of the outer surface adjacent to and below the third portion thereof;

(E) Coating the outer surface and the remaining coating of removable bond preventing agent with an overcoat layer of a suitable film forming polymeric bonding composition; and (F) Curing the overcoat layer.

Following those steps, methods of the present invention include the following steps:

(A) Securing an end piece to the end of the tube furthest from the first lumen access opening;

(B) Simultaneously testing the balloon portion of the resulting catheter and substantially removing the removable preventing bond agent from the first portion of the outer surface and the first lumen access opening;

(C) Further testing the catheter capillary lumen and the balloon portion for leaks;

(D) Punching a second lumen access opening in an exterior surface of the catheter to communicate with the second lumen;

(E) Packaging the resulting sleeved Foley catheters; and (F) Sterilizing the sleeved Foley catheters.

In another preferred embodiment of the present invention, following the securing of a plurality of intermediate tubes 3' to the transportable pallet 24', balloon catheters are produced as follows:

(A) The pallet 24' is stopped over a first tank 33, which contains white USP petrolatum heated to about 60° C. That tank 33 is then raised so as to immerse the intermediate tubes 3' into the petrolatum to such a depth that the petrolatum reaches the proximal end of the desired resilient sleeve location proximate the dashed line designated A in FIG. 15. The dip tank 33 is then lowered and a portion of the outer surface 14' of the intermediate tubes 3' are coated with petrolatum. This portion extends from the general point at which the proximal end of the resilient sleeve 44' will begin, to the distal end 2a' of the tip 20' of each intermediate tube 3'. In other embodiments, this step can be repeated to increase the thickness of the lubricant coating 38', as well as the ultimate volume of the sleeve cavity 45' and the size of the outside diameter of the catheter 5' proximate the sleeve 44'.

(B) The steps outlined in paragraphs B, C and D of Example I presented hereinabove, are then followed generally as outlined in Example I.

(C) The pallet 24' is then stopped over a fifth dip tank 41, which contains a liquid soap (Liquid Ivory Soap from Proctor & Gamble Co., Cincinnati, Ohio 45202). The soap is held at room temperature (between about 60°-80° F., preferably 65°-72° F.). The fifth dip tank 41 is raised so as to immerse the intermediate tubes 3' into the liquid soap so that the soap coats the tubes 3' up to the dashed line designated by the letter C in FIG. 18. The dip tank 41 is then lowered and the liquid soap forms a semi-solid coating 40' on the outer surface 14' of each of the intermediate tubes 3' extending from line designated C to the distal end 20a' of the tip 20' of each of the intermediate tubes 3'.

(D) The pallet 24 is then automatically advanced and stopped over a sixth dip tank 43 which contains an aqueous solution containing a trace of a suitable wetting agent or surfactant. In a preferred embodiment, three gallons of water is mixed with two ounces of a suitable surfactant. The surfactant will generally be less than one percent of the total volume of the solution. A sixth dip tank 43 is then raised so as to immerse the intermediate tubes 3' in the aqueous fluid up to the dashed line designated by the letter D in FIGS. 18 and 19. The sixth dip tank 43 is then lowered and the semi-solid liquid soap coating the portion 14a' of the outer surface 14' below the dashed line designated D is substantially removed.

(E) The pallet 24' is then automatically advanced and stopped over a seventh dip tank 47 containing water. The seventh dip tank 47 is then raised and the intermediate tubes 3' are immersed in the water up to the line designated D as in the prior dipping step. The seventh dip tank 47 is then lowered and virtually all of the liquid soap is removed from the portion 14a' of the outer surface 14' below the line designated D.

(F) The pallet 24' is then automatically advanced and stopped over a eighth dip tank 49 containing a low-solids silicone rubber solvent dispersion which is effective to minimize any disruption of the integrity of the liquid soap coating 40' remaining on each of the intermediate tubes proximate the portion 14c' of the outer surface 14' where the balloon cavity 54 will be created during subsequent dipping steps (the portion between the dashed lines designated C and D). The eighth tank 49 is then raised to immerse intermediate tubes 3' in the silicone rubber dispersion. It will be appreciated that any suitable solvent for providing a suitable dispersion of silicone rubber and coating the particular lubricating agent may be used. It is also believed to be possible to use aqueous solvents, however, they are not preferred at present. It will also be appreciated that this step can be repeated at subsequent intervals, preferably long enough to permit significant solvent evaporation, to add to the thickness of the overcoat layer 42 and the balloon portion 58 of the overcoat layer 42. However, further steps, involving different solutions can also follow.

(G) The fourth dip tank 39 is then lowered and the silicone rubber, coating portions of the outer surface 14' as well as the coating of petrolatum 38' and the coating of soap 40', is allowed to dry. The pallet 24' is then advanced again to a ninth dip tank 51 containing a different silicone rubber dispersions having a solids content which is higher than the solids content in the eighth dip tank 49. The intermediate tubes 31 are immersed again in the subsequent silicone rubber dispersion when the ninth dip tank 51 is raised. The ninth dip tank 51 is then lowered, and the silicone rubber, coating the tubes 3' is allowed to dry.

(H) The pallet 24' is then automatically advanced again to a tenth dip tank 53 containing a silicone rubber dispersion including a silicone rubber which provides a high sheen and a smooth texture surface. The tubes 3' are dipped again as before and the tenth dip tank 53 is then lowered and the silicone rubber coating the tubes 3' is allowed to dry.

(G) The pallet 24' is then advanced through a drying step followed by a heat cure step, and each completed sleeved balloon catheter 5' is then secured to an end piece 46', tested, provided with a fluid conduit access opening 56', packaged and sterilized.

The automated system that Applicants claim will permit completed sleeved Foley catheters 4' to be manufactured at the rate of about 1,600 catheters per hour. Because virtually no handwork is involved in the balloon and sleeve construction, the catheters 4' produced will be consistent and of very high quality. The exterior surface 62' is smoother than hand-glued balloons, and the outside diameter of the balloon portion 58' is essentially identical to the outside diameter of other portions of the completed Foley catheters 4'. It will be appreciated that larger outside diameter balloon portions are undesirable since they are somewhat more difficult to insert and withdraw, and cause additional trauma upon withdrawal. In addition, by eliminating the hand labor involved in adhering the balloon portion 58' to the intermediate tube 3' in the manufacture of silicone rubber balloon catheters 5', by specifically eliminating the separate step of fabricating the balloon portion, which also requires hand labor, and by eliminating the significant impact on yield resulting from hand processing errors, the applicants' new process will permit direct production cost for silicone rubber balloon catheters of all types to be reduced by about 25-50% over the cost estimate for the prior art silicone rubber balloon catheters.

It is to be understood, however, that even though numerous characteristics and advantages of the present invention have been set forth in the foregoing description, together with details of the structure and function of the invention, the sequence or order of the specific steps, or the actual compositions, solvents, temperatures, environmental conditions and the like employed for each step, it will be appreciated the disclosure is illustrative only, and that changes may be made in detail, especially in matters of shape, size, arrangement of parts or sequence or elements of events within the principles of the invention to the full extent indicated by the broad general meaning of the terms in which the appended claims are expressed.

What is claimed is:

1. An elongated catheter comprising an interior surface and an exterior surface, said interior surface defining a first lumen passing through said catheter, said catheter further including an enclosed cavity between said interior and exterior surfaces which encircles a portion of said first lumen, said enclosed cavity having an inner wall and an outer wall, said outer wall being a resilient sleeve which can stretch generally independently of said inner wall, said enclosed cavity containing an amount of a suitable lubricating substance effective to permit said sleeve to slide along an outer surface of the inner wall while in lubricated contact therewith when stretched independently of said inner wall, wherein the inner wall and the outer wall are joined together at distal and proximal ends of said enclosed cavity; said catheter further including a second lumen, an inflatable balloon and a balloon cavity, the second lumen communicating with the balloon cavity, wherein fluid can pass into the balloon cavity from the second lumen so as to inflate the inflatable balloon.

2. The elongated catheter of claim 1 wherein the inner wall has a greater thickness than the outer wall.

3. The elongated catheter of claim 2 wherein said catheter is made of a flexible elastomeric material, and wherein the lubricating substance is enclosed within the cavity.

4. The elongated catheter of claim 3 wherein the outer wall is easier to stretch than the inner wall.

5. The elongated catheter of claim 1 wherein the lubricating substance is any biocompatible lubricating substance which is effective to permit respective polymeric surfaces to slide generally evenly with respect to one another when in lubricated contact with each other.

6. The elongated catheter of claim 5 wherein the lubricating substance is petrolatum.

7. An elongated catheter comprising an interior surface defining a first lumen, an expandable balloon having an expandable balloon cavity a second lumen in communication with the expandable balloon cavity, an exterior surface, and an enclosed sleeve cavity located between the respective interior and exterior surfaces and encircling the first lumen in a position removed from the expandable balloon cavity, said catheter further comprising a resilient sleeve portion encircling the first lumen and said sleeve cavity, said sleeve cavity containing a lubricating substance.

8. The elongated catheter of claim 7 wherein the lubricating substance is any biocompatible lubricating substance which is effective to permit respective polymeric surfaces to slide generally evenly with respect to one another when in lubricated contact with each other.

9. The elongated catheter of claim 8 wherein the lubricating substance is petrolatum.

10. An elongated catheter comprising a tube having an inner surface and an outer surface, said inner surface defining a first lumen, said catheter further comprising an overcoat layer including a resilient sleeve portion encircling the outer surface of the tube, wherein the overcoat layer is fixed to the outer surface at distal and proximal ends of an enclosed sleeve cavity defined by an interior surface of the sleeve portion and a sleeve area of the outer surface proximate the sleeve portion, wherein the sleeve cavity contains a lubricating substance effective to permit said resilient sleeve portion to slide along and with respect to the sleeve area of the outer surface while in lubricated contact therewith and when stretched independently thereof, said elongated catheter further comprising a second lumen and a inflatable balloon portion removed from the sleeve portion, said balloon portion including an expandable balloon cavity in communication with said second lumen.

11. The elongated catheter of claim 10 wherein the lubricating substance is any biocompatible lubricating substance which is effective to permit respective polymeric surfaces to slide generally evenly with respect to one another when in lubricated contact with each other.

12. The elongated catheter of claim 11 wherein the lubricating substance is petrolatum.

13. An elongated catheter comprising a tube and an overcoat layer, said tube having an inner surface and an outer surface, said inner surface defining a first lumen, said overcoat layer including a resilient sleeve encircling the outer surface of the tube proximate a first portion of the outer surface, said overcoat layer being fixed to said outer surface proximate second and third portions of said outer surface which are located opposite one another in respect to and on either side of said first portion, said resilient sleeve of said overcoat layer and said first portion of said outer surface cooperating to define a sleeve cavity, wherein the sleeves cavity contains a lubricating substance effective to permit said resilient sleeve to slide along and in respect said first portion of the outer surface while in lubricated contact therewith and when stretched independently thereof; said tube having a second lumen and a first lumen access opening in a fourth portion of said outer surface removed from the first portion thereof, said overcoat layer further including a resilient balloon proximate said fourth portion, wherein said balloon and said fourth portion of the outer surface cooperate to define a balloon cavity, wherein said balloon cavity communicates with said first lumen via said first lumen access opening, and wherein said overcoat layer is fixed to said outer surface proximate a fifth portion of said outer surface, wherein said fifth portion and said third portion of the outer surface are located opposite one another in respect to and on either side of said fourth portion.

14. The elongated catheter of claim 13 wherein the lubricating substance is any biocompatible lubricating substance which is effective to permit respective polymeric surfaces to slide generally evenly with respect to one another when in lubricated contact with each other.

15. The elongated catheter of claim 14 wherein the lubricating substance is petrolatum.

16. An elongated catheter comprising an interior surface and an exterior surface, said interior surface defining a first lumen passing through said catheter, said catheter further including an enclosed cavity between said interior and exterior surfaces which encircles a portion of said first lumen, said cavity having an inner wall and an outer wall, said outer wall being a resilient sleeve which can stretch generally independently of said inner wall, said inner and outer walls being provided with friction reducing means for reducing friction between surfaces of the inner and outer wall which cooperate to define the cavity, wherein said friction reducing means are effective to permit surfaces of said inner and outer walls to slide evenly with respect to one another when contacting each other, wherein the inner wall and outer wall are jointed together at distal and proximal ends of said cavity, said catheter further including a second lumen, an inflatable balloon and a balloon cavity, the second lumen communicating with the balloon cavity, wherein fluid can pass into the balloon cavity from the second lumen so as to inflate the inflatable balloon.

17. The elongated catheter of claim 16 wherein the inner wall has a greater thickness than the outer wall.

18. The elongated catheter of claim 17, said friction reducing means including a suitable lubricating substance effective to permit said sleeve to slide along an outer surface of the inner wall while in lubricated contact therewith when stretched independently of said inner wall.

19. The elongated catheter of claim 18 wherein the lubricating substance is any biocompatible lubricating substance which is effective to permit respective polymeric surfaces to slide generally evenly with respect to one another when in lubricated contact with each other.

20. The elongated catheter of claim 19 wherein the lubricating substance is petrolatum.

21. An elongated catheter comprising an interior surface and an exterior surface, said interior surface defining a first lumen passing through said catheter, said catheter further including an enclosed cavity between said interior and exterior surfaces which encircles a portion of said first lumen, said cavity having an inner wall and an outer wall, said outer wall being a resilient sleeve which can stretch generally independently of said inner wall, said cavity containing a substance which is effective to provide for a separation between said inner wall and said outer wall and cushion the outer wall from impacting against the inner wall, where as the cavity has a volume which can increase the outside diameter of the catheter proximate the sleeve at least about 10 percent over the outside diameter of the catheter if the cavity was empty, said catheter further including a second lumen, an inflatable balloon and a balloon cavity, the second lumen communicating with the balloon cavity, wherein fluid can pass into the balloon cavity from the second lumen so as to inflate the inflatable balloon.

22. A method of catheterizing a person having an internal passageway defined by internal walls within the person's body, said method comprising the steps of:
(a) providing an elongated catheter including an interior surface and an exterior surface, said interior surface defining a lumen passing through said catheter, said catheter further including an enclosed cavity between said interior and exterior surfaces which encircles a portion of said lumen, said cavity having an inner wall and an outer wall, said outer wall being a resilient sleeve which can stretch generally independently of said inner wall, wherein the cavity contains an amount of an appropriate substance which is sufficient to provide a separation between the inner wall and the outer wall; and
(b) inserting the catheter into the passageway such that a portion of the exterior surface proximate the sleeve is in contact with at least one internal wall, and wherein the inner wall can move within the passageway without moving the portion of the exterior surface of the catheter proximate the sleeve in contact with the at least one internal wall.

23. A method of catheterizing a person having an internal passageway defined by internal walls within the person's body, said method comprising the steps of:
(a) providing an elongated catheter including an interior surface and an exterior surface, said interior surface defining a lumen passing through said catheter, said catheter further including an enclosed cavity between said interior and exterior surfaces which encircles a portion of said lumen, said cavity having an inner wall and an outer wall, wherein the outer wall is a conformable sleeve having a surface which generally conforms to surfaces of the adjacent inner wall with which it comes into contact, wherein the cavity contains an amount of an appropriate, displaceable substance which is sufficient to provide a separation between the inner wall and the outer wall which cushions the inner wall from impacts on the outer wall; and
(b) inserting the catheter into the passageway such that a portion of the exterior surface proximate the sleeve is in contact with at least one internal wall.

24. An elongated catheter comprising a tube and an overcoat layer, said tube having an inner surface and an outer surface, said inner surface defining a first lumen, said overcoat layer including a resilient sleeve encircling the outer surface of the tube proximate a first portion of the outer surface, said overcoat layer being fixed to said outer surface proximate second and third portions of said outer surface which are located opposite one another in respect to and on either side of said first portion, said resilient sleeve of said overcoat layer and said first portion of said outer surface cooperating to define an enclosed sleeve cavity, wherein the sleeve cavity contains a complaint substance which allows the resilient sleeve to conform to adjacent surfaces with which it comes into contact and permits said resilient sleeve to slide along and in respect said first portion of the outer surface while in lubricated contact therewith and when stretched independently thereof; said tube having a second lumen and a first lumen access opening in a further portion of said outer surface removed from the first portion thereof, said overcoat layer further including a resilient balloon proximate said fourth portion, wherein said balloon and said fourth portion of the outer surface cooperate to define a balloon cavity, wherein said balloon cavity communicates with said first lumen via said first lumen access opening, and wherein said overcoat layer is fixed to said outer surface proximate a fifth portion of said outer surface, wherein said fifth portion and said third portion of the outer surface are located opposite one another in respect to and on either side of said fourth portion.

25. The elongated catheter of claim 24, wherein the compliant substance is a lubricating substance effective to permit said resilient sleeve to slide along and in respect said first portion of the outer surface while in lubricated contact therewith.

26. The elongated catheter of claim 25, wherein the lubricating substance is petrolatum.

27. An elongated catheter comprising an interior surface defining a first lumen, a second lumen in communication with an expandable balloon cavity, an exterior surface, and an enclosed sleeve cavity located between the respective interior and exterior surfaces and encircling the first lumen in a position removed from the balloon cavity, said catheter further comprising a resilient sleeve portion encircling the first lumen and said sleeve cavity and an expandable balloon portion encircling the expandable balloon cavity and located in a position removed from said sleeve portion and contiguous with an outer surface of the resilient sleeve portion, and said sleeve cavity containing a compliant substance which allows the resilient sleeve portion to conform to adjacent surfaces with which it comes into contact.

28. The elongated catheter of claim 27 wherein the compliant substance is a biocompatible lubricating substance which is effective to permit the resilient sleeve portion to slide along, and with respect to, said inner wall while in lubricated contact therewith.

29. The elongated catheter of claim 28 wherein the biocompatible lubricating substance is petrolatum.

* * * * *

UNITED STATES PATENT AND TRADEMARK OFFICE
CERTIFICATE OF CORRECTION

PATENT NO. : 5,098,379
DATED : March 24, 1992
INVENTOR(S) : Conway et al.

It is certified that error appears in the above-indentified patent and that said Letters Patent is hereby corrected as shown below:

TITLE PAGE

In the Abstract, line 6, please insert --a portion-- after the word "encircles".

In the Abstract, line 15, "end" should read --and--.

IN THE DRAWINGS

In Figure 27, add reference numeral "21''''" as shown on attached Figure.

In column 1, line line 57, "to" should read --of--.

In column 5, line 45, delete "be" after the word "would".

In column 6, line 11, "coating" should read --coated--.

In column 8, line 23, insert --,-- after the words "(not shown)".

In column 9, line 41, insert --,-- after the words "(not shown)".

In column 10, line 27, "24" should read --24'--.

In column 10, line 56, insert --,-- after the words "(not shown)".

In column 12, line 57, insert --,-- after the words "(not shown)".

UNITED STATES PATENT AND TRADEMARK OFFICE
CERTIFICATE OF CORRECTION

PATENT NO. : 5,098,379
DATED : March 24, 1992
INVENTOR(S) : Conway et al.

It is certified that error appears in the above-indentified patent and that said Letters Patent is hereby corrected as shown below:

In column 11, line 68, delete "an" after the word "and".

In column 13, line 16, insert --to-- after the word "catheter".

In column 13, line 23, insert --,-- after the words "(not shown)".

In column 13, line 28, insert --,-- after the words "(not shown)".

In column 13, lines 49 and 50, insert --,-- after the words "(not shown)".

In column 14, line 18, "accessing" should read --access--.

In column 14, lines 41, 47 and 48, insert --,-- after the words "(not shown)".

In column 14, line 55, "25'" should read --25--.

In column 15, line 3, insert --,-- after the words "(not shown)".

In column 15, line 19, "26'" should read --26--.

In column 15, line 44, "a" should read --an--.

In column 19, line 41, "rubber solvent" should read --rubber/solvent--.

UNITED STATES PATENT AND TRADEMARK OFFICE
CERTIFICATE OF CORRECTION

PATENT NO. : 5,098,379
DATED : March 24, 1992
INVENTOR(S) : Conway et al.

It is certified that error appears in the above-indentified patent and that said Letters Patent is hereby corrected as shown below:

In column 19, line 40, "a" should read --an--.

In column 19, line 64, delete "a" after the word "containing".

In column 20, line 39, "estimate should read --estimated--.

In column 22, claim 13, line 9, "sleeves" should read --sleeve--.

In column 24, claim 24, line 23, "further" should read --fourth--.

Signed and Sealed this

Fourth Day of October, 1994

Attest:

BRUCE LEHMAN

*Attesting Officer*      *Commissioner of Patents and Trademarks*